United States Patent
Narendran et al.

(10) Patent No.: US 11,975,106 B2
(45) Date of Patent: *May 7, 2024

(54) USES OF HALOGENATED XANTHENES IN ONCOLOGY AND VIROLOGY

(71) Applicants: Provectus Pharmatech, Inc., Knoxville, TN (US); UTI Limited Partnership, Calgary (CA)

(72) Inventors: Aru Narendran, Calgary (CA); Edward V. Pershing, Knoxville, TN (US); Dominic Rodrigues, Knoxville, TN (US); Bruce Horowitz, Knoxville, TN (US); Eric A. Wachter, Oak Ridge, TN (US)

(73) Assignees: Provectus Pharmatech, Inc., Knoxville, TN (US); UTI Limited Partnership, Calgary (CA)

( * ) Notice: Subject to any disclaimer, the term of this patent is extended or adjusted under 35 U.S.C. 154(b) by 103 days.

This patent is subject to a terminal disclaimer.

(21) Appl. No.: 17/212,723

(22) Filed: Mar. 25, 2021

(65) Prior Publication Data

US 2021/0299083 A1    Sep. 30, 2021

Related U.S. Application Data

(60) Provisional application No. 63/000,231, filed on Mar. 26, 2020.

(51) Int. Cl.
| | |
|---|---|
| *A61K 9/28* | (2006.01) |
| *A61K 9/00* | (2006.01) |
| *A61K 31/352* | (2006.01) |
| *A61K 31/706* | (2006.01) |
| *A61K 45/06* | (2006.01) |
| *A61K 47/14* | (2017.01) |
| *A61P 35/00* | (2006.01) |

(52) U.S. Cl.
CPC .......... *A61K 9/2833* (2013.01); *A61K 9/0053* (2013.01); *A61K 31/352* (2013.01); *A61K 31/706* (2013.01); *A61K 45/06* (2013.01); *A61K 47/14* (2013.01); *A61P 35/00* (2018.01)

(58) Field of Classification Search
CPC .. A61K 9/2833; A61K 9/0053; A61K 31/352; A61K 31/706; A61K 45/06; A61K 47/14; A61K 9/0056; A61K 9/2018; A61K 9/2027; A61K 9/2846; A61K 9/4866; A61K 9/4891; A61K 9/5026; A61K 9/5042; A61K 9/5078; A61K 47/26; A61K 47/32; A61P 35/00
See application file for complete search history.

(56) References Cited

U.S. PATENT DOCUMENTS

| | | |
|---|---|---|
| 3,859,286 A | 1/1975 | Fleming et al. |
| 4,599,231 A | 7/1986 | Milich et al. |
| 5,180,806 A | 1/1993 | Dillner et al. |
| 5,998,597 A | 12/1999 | Fisher et al. |
| 6,331,286 B1 | 12/2001 | Dees et al. |
| 6,493,570 B1 | 12/2002 | Dees et al. |
| 6,942,866 B2 | 9/2005 | Birkett |
| 7,390,668 B2 | 6/2008 | Dees et al. |
| 7,648,695 B2 | 1/2010 | Dees et al. |
| 8,017,127 B2 | 9/2011 | Birkett |
| 8,530,675 B2 | 9/2013 | Singer et al. |
| 8,557,298 B2 | 10/2013 | Scott et al. |
| 8,974,363 B2 | 3/2015 | Dees et al. |
| 9,107,887 B2 | 8/2015 | Eagle et al. |
| 9,273,022 B2 | 3/2016 | Singer et al. |
| 9,422,260 B2 | 8/2016 | Singer et al. |
| 9,808,524 B2 | 11/2017 | Eagle et al. |
| 9,839,688 B2 | 12/2017 | Eagle et al. |
| 10,130,658 B2 | 11/2018 | Singer et al. |
| 10,471,144 B2 | 11/2019 | Eagle et al. |
| 2005/0249739 A1* | 11/2005 | Marasco ................ C07K 16/10 530/388.3 |

(Continued)

FOREIGN PATENT DOCUMENTS

| | | | |
|---|---|---|---|
| EP | 0471794 | * | 10/1996 |
| EP | 0471794 B1 | | 10/1996 |

(Continued)

OTHER PUBLICATIONS

Ghahsare, Current Organic Synthesis, 2019, 16, 1-7 (Year: 2019).*
Maia, European Journal of Medicinal Chemistry, 210, 2021, 113085 (Year: 2021).*
Yang, H. et al, "Design of Wide-Spectrum Inhibitors Targeting Coronavirus Main Proteases," PLOS Biology, vol. 3, issue 10, e324, Oct. 2005, pp. 1742-1752.
Zhang, L. et al, "Crystal Structure of SARS-CoV-2 Main Protease Provides a Basis for Design of Improved α-Ketoamide Inhibitors," Science 10.1126/science.abb3405 (Mar. 20, 2020).

(Continued)

*Primary Examiner* — Susanna Moore
*Assistant Examiner* — Luisalberto Gonzalez
(74) *Attorney, Agent, or Firm* — Husch Blackwell LLP

(57) ABSTRACT

A method for treating a viral infection of a mammalian subject that comprises administering a virus-inhibiting amount of a halogenated xanthene, a pharmaceutically acceptable salt, an alkyl ester or amide or aromatic ester or amide derivative thereof as disclosed within, to that mammalian subject. A method of inducing a type I interferon response in a mammalian subject that presents with a microbial infection, cancerous tumor or hematological malignancy that comprises administering an amount of a halogenated xanthene as discussed above, effective to induce the type I interferon response. A method of enhancing a mammalian immunogen-specific immune response that comprises contacting mammalian cells, in vivo or present in a mammalian cell growth supporting medium, with an adjuvant-effective amount of a halogenated xanthene as discussed above, and an immunogen to which that response is to be enhanced.

25 Claims, 30 Drawing Sheets

(56) References Cited

U.S. PATENT DOCUMENTS

| | | | | |
|---|---|---|---|---|
| 2012/0157435 A1* | 6/2012 | Hurt | ................ | A61P 31/18 514/218 |
| 2019/0350893 A1 | 11/2019 | Singer et al. | | |

FOREIGN PATENT DOCUMENTS

| | | |
|---|---|---|
| FR | A-2118030 | 7/1972 |
| GB | 1 353 536 | 5/1974 |
| JP | 4507403 A | 12/1992 |
| JP | 2004503592 A | 2/2004 |
| WO | 20020062333 A1 | 8/2002 |
| WO | 2020028532 A1 | 2/2020 |

OTHER PUBLICATIONS

Xue, X. et al, "Structures of two Coronavirus Main Proteases: Implications for Substrate Binding and Antiviral Drug Design," Journal of Virology, vol. 82, No. 5, Mar. 2008, pp. 2515-2527.

Jin, Z. et al, "Structure-Based Drug Design, Virtual Screening and High-Throughput Screening Rapidly Identify Antiviral Leeds Targeting COVID-19," BioRxiv, https://doi.org/10.1101/2020.02.26. 964882, Feb. 5, 2020 (posted Feb. 27, 2020).

Padhi, A.K. et al, "Rational Design of the Remdesivir Binding Site in the RNA-Dependent RNA-Polymerase of SARS-CoV-2: Implications for Potential Resistance," BioRxiv, p. 4, preprint doi: https://doi.org/10.1101/2020.06.27.174896; (posted Jun. 29, 2020).

Tempestilli, M. et al, "Pharmacokentics of Remdesivir and GS-441524 in two Critically ill Patients who Recovered from COVID-19," Journal of Antimicrobial Chemotherapy, doi:10.1093/jac/dkaa239, pp. 1-4, (accepted May 14, 2020).

Tchesnokov, E.P. et al, "Template-Dependent Inhibition of Coronavirus RNA-Dependent RNA Polymerase by Remdesivir Reveals a Second Mechanism of Action," J. Bio Chem, vol. 295, No. 47, Sep. 23, 2020, pp. 16156-16165.

Li, Y. et al, "An Exploratory Randomized, Controlled Study on the Efficacy of and Safety of of lopinavir/ritonavir or arbidol Treating Adult Patients Hospitalized with Mild/moderate COVID-19 (ELACOI)," medRxiv, Mar. 19, 2020; medRxiv preprint doi: https://doi.org/10. 1101/2020.03.19.20038984.

Kupferschmidt, K. et al, "Race to Find COVID-19 Treatments Accelerates," Science, vol. 367, issue 6485, Mar. 27, 2020, pp. 1412-1413; DOI: 10.1126/Science.367.6485.1412.

Ortolani, C. et al, "Hydroxychloroquine and Dexamethasone in COVID-19: Who Won and Who Lost?" Clinical and Molecular Allergy, vol. 18:17, 2020; https://doi.org/10.1186/s12948-020-00132-7.

Horby, P.W. et al, "Tocilizumab in Patients Admitted to Hospital with 3 COVID-19 (Recovery): Preliminary Results of a Randomized, Controlled, Open-label, Platform Trial," medRxiv, Feb. 11, 2021; medRxiv preprint doi: https://doi.org/10.1101/2021.02.11. 21249258.

De Andrea, M. et al, "The Interferon System: An Overview," European Journal of Paediatric Neurology, vol. 6, suppl. A, A41-A46, 2002; DOI: 10.1053/ejpn.2002.0573.

Parkin, J. et al, "An Overview of the Immune System," The Lancet, vol. 357, pp. 1777-1789, Jun. 2, 2001.

Motani, K. et al, "Activation of Stimulator of Interferon Genes (STING) Induces ADAM17-mediated Shedding of the Immune Semaphorin SEMA4D," J. Biol. Chem., vol. 293, No. 20, pp. 7717-7726, 2018; doi.10.1074/jbc.RA118.002175.

Sa Ribero, M. et al, "Interplay Between SARS-CoV-2 and the Type I Interferon Response," PLOS Pathogens, vol. 16, No. 7, 22 pgs., Jul. 29, 2020; https://doi.org/10.1371/journal.ppat.1008737.

Sun, W. et al, "ERIS, an Endoplasmic Reticulum IFN Stimulator, Activates Innate Immune Signaling Through Dimerization," PNAS, vol. 106, No. 21, pp. 8653-8658, May 26, 2009; www.pnas.org/cgi/doi/10.1073/pnas.0900850106.

Abe, T. et al, "STING Recognition of Cytoplasmic DNA Instigates Cellular Defense," Molecular Cell, vol. 50 (1), 5-15, Apr. 11, 2013; http://dx.doi.org/10.1016/j.molcel.2013.01.039.

Barber, G.N, "STING: Infection, Inflammation and Cancer," Nature, vol. 15, No. 12, pp. 760-770, Dec. 2015; doi:10.1038/nri3921.

Sali, T.M. et al, "Characterization of a Novel Human-Specific STING Agonist that Elicits Antiviral Activity Against Emerging Alphaviruses," PLOS Pathogens, pp. 1-30, Dec. 8, 2015; DOI: 10.1371/journal.ppat.1005324.

Guo, F. et al, "STING Agonists Induce an Innate Antiviral Immune Response against Hepatitis B Virus," Antimicrobial Agents and Chemotherapy, vol. 59, No. 2, pp. 1273-1281, Feb. 2015; http://dx.doi.org/10.1128/AAC.04321-14.

Conlon, J. et al, "Mouse, but not Human STING, Binds and Signals in Response to the Vascular Disrupting Agent 5,6-Dimethylxanthenone-4-Acetic Acid," Journal of Immunology, 2013;190:5216-5225; doi: 10.4049/jimmunol.1300097.

Liu, S. et al, "STING Signaling Promotes Apoptosis, Necrosis, and Cell Death: An Overview and Update," Mediators of Inflammation, vol. 2018, Article ID 1202797, 4 pages; https://doi.org/10.1155/2018/1202797.

Simon, A.K. et al, "Evolution of the Immune System in Humans from Infancy to Old Age," Proc. R. Soc. B 282: 20143085; 2015; http://dx.doi.org/10.1098/rspb.2014.3085.

Liu, H. et al, "Intralesional Rose Bengal in Melanoma Elicits Tumor Immunity via Activation of Dendritic Cells by the Release of High Mobility Group Box 1," Oncotarget, vol. 7, No. 25, pp. 37893-37905; May 9, 2016.

Krueger, J.G. et al, "P013 Immune Modulation by Topical PH-10 Aqueous Hydrogel (rose Bengal disodium) in Psoriasis Lesions," Psoriasis from gene to clinic, Programme & Abstracts Nov. 30-Dec. 2, 2017 p. 79, 8th International Congress, The Queen Elizabeth II Conference Centre, London, UK Nov. 30-Dec. 2, 2017.

Tsao, S. et al, "Protein-Mediated Hepatic Uptake of Rose Bengal in Analbuminemic Mutant Rats (NAR)," Drug Metabolism and Disposition, vol. 16, No. 3, pp. 482-489, 1988; 0090-9556/88/1603-0482S02.00/0.

Luxon, B.A. et al, "Hepatic Transport of Rose Bengal by Perfused Rabbit Liver: The Effect of Albumin Binding on the Unidirectional Rate Constants," The Journal of Pharmacology and Experimental Therapeutics, vol. 275, No. 1, pp. 296-305, 1995.

Meurman, L., "Acta Medica Scan," Supp 167, Chapters I, III, V, VII, X and XII (1960).

Green, F.J., Sigma-Aldrich Handbook of Stains, Dyes and Indicators, Aldrich Chemical Company, Inc., Milwaukee, WI, pp. 637-638 (1990).

Delprat, G.D. et al, "A New Liver Function Test: The Elimination of Rose Bengal When Injected Into the Circulation of Human Subjects," Achives of Internal Medicine, vol. 34, pp. 533-541, 1924.

Taplin, G.V. et al, "Radioactive Rose Bengal Uptake-Excretion Test,", The Journal of Laboratory and Clinical Medicine, vol. 45, No. 5, pp. 665-678, 1955.

Yoshimoto, M. et al, "Effects of Coal Tar Dyes on Viability, and RNA and Protein Syntheses in Isolated Rat Hepatocytes," J. Food Hyg. Soc. Japan vol. 25, No. 4, pp. 347-351, Aug. 1984.

Graham, B.S. et al, "Structure-Based Vaccine Antigen Design," Annu Rev Med., vol. 70, pp. 91-104, Jan. 27, 2019; doi:10.1146/annurev-med-121217-094234.

Wrapp, D. et al, "Cryo-EM Structure of the 2019-nCoV Spike in the Profusion Conformation," Science, vol. 367, pp. 1260-1263, Mar. 13, 2020.

Gordon, D.E. et al, "A SARS-CoV-2-Human Protein-Protein Interaction Map Reveals Drug Targets and Potential Drug-Repurposing," (bioRxiv preprint doi: https://doi.org/10.1101/2020.03.22.002386); Nature, vol. 583, pp. 459-468, Apr. 30, 2020.

Tseng, C. et al, "Apical Entry and Release of Severe Acute Respiratory Syndrome-Associated Coronavirus in Polarized Calu-3 Lung Epithelial Cells," Journal of Virology, vol. 79, No. 15, pp. 9470-9479, Aug. 2005; doi:10.1128/JVI.79.15.9470-9479.2005.

Swift, L. et al, "Potent in vitro and Xenograft Antitumor Activity of a Novel Agent, PV-10, Against Relapsed and Refractory Neuroblastoma," OncoTargets and Therapy, vol. 12, pp. 1293-1307, 2019.

(56) References Cited

OTHER PUBLICATIONS

Swift, L. et al, "In Vitro Activity and Target Modulation of PV-10 Against Relapsed and Refractory Pediatric Leukemia," Blood (2018) 132 (Supplement 1): 5207; https://doi.org/10.1182/blood-2018-99-119438.
Sheahan, T.P. et al, "Broad-Spectrum Antiviral GS-5734 Inhibits both Epidemic and Zoonotic Coronaviruses," Science Translational Medicine, vol. 9, No. 396, eaal3653, pp. 1-10, Jun. 28, 2017; doi: 10.1126/scitranslmed.aal3653.
Remdesivir; Wikipedia, Mar. 25, 2020, pp. 1-8; retrieved Jul. 6, 2021, (https://en.wikipedia.org/w/index.php?title=Remdesivir&oldid=9472341637).
International Search Report re application No. PCT/US2021/24185, dated Aug. 9, 2021.
Written Opinion re application No. PCT/US2021/24185, dated Aug. 9, 2021.
Handbook of Chemistry and Physics, 54th Edition, R. C. Weast, ed. CRC Press, p. C-37 (1973-1974).
Karpinska, J. et al., "Analytical Properties of 2- and 10-Distributed Phenothiazine Derivatives," Anal Sci 12:161-170 (Apr. 1996). https://doi.org/10.2116/analsci.12.161.
Ishikawa, H. et al, "STING an Endoplasmic Reticulum Adaptor that Facilitates Innate Immune Signaling," Nature, vol. 455, No. 2713, pp. 674-678, Oct. 2, 2008. doi:10.1038/nature07317.
Howard, S.C. et al, "The Tumor Lysis Syndrome," New England Journal of Medicine, vol. 364, No. 19, pp. 1844-1854, May 12, 2011. doi:10.1056/NEJMra0904569.
Berge, S.M. et al, "Pharmaceutical Salts," Journal of Pharmaceutical Sciences, vol. 66, No. 1, pp. 1-19, Jan. 1977.
*Catalog Handbook of Fine Chemicals*, Aldrich Chemical Company, Milwaukee, WI, pp. 809 & 1734 (1998-1999).
Swartz et al., *Proc Soc Exp Biol Med* 161(2):204-209 (1979).
Badylak et al., *J Clin Microbiol* 17(2):374-376 (1983).
Azher et al., *Clin Opthalmol* 11:185-191, 187 (2017).
Abstract: Nordyke et al., *JAMA*, 170(10):1159-1164 (1959).
Richard L. Robbins, *Subtests of "Nonobviousness"; A Nontechnical Approach to Patent Validity*, 112 U. Pa. L. Rev. 1169 (1964).
Costa et al., *Viruses* 4:1034-1074, 1052 (2012).
Fernandez-Perez et al., *ACS Omega* 5:29801-29815 (2020).
Jockusch et al., *Proc Natl Acad Sci, USA*, 93:7446-7451 (1996).
Alarcon et al., *ACS Omega* 2:6646-6657 (2020).
Guruprasad, *Prog Biophys Mol Biol* 161:39-53 (2021), (available on line Oct. 31, 2020; document E-14).
Mukherjee et al., *Encyclopedia of Cell Biology*, "Proteases of SARS Coronaviruses", $2^{nd}$ ed, vol. 1, Bradshaw et al. eds., Elsevier, Amsterdam, Netherlands, 930-941 (2023).
Office Action re Japanese application No. JP 2022-558583, dated Oct. 31, 2023.
Extended European Search Report re application No. EP 12774987.8, dated Jan. 30, 2024.

\* cited by examiner

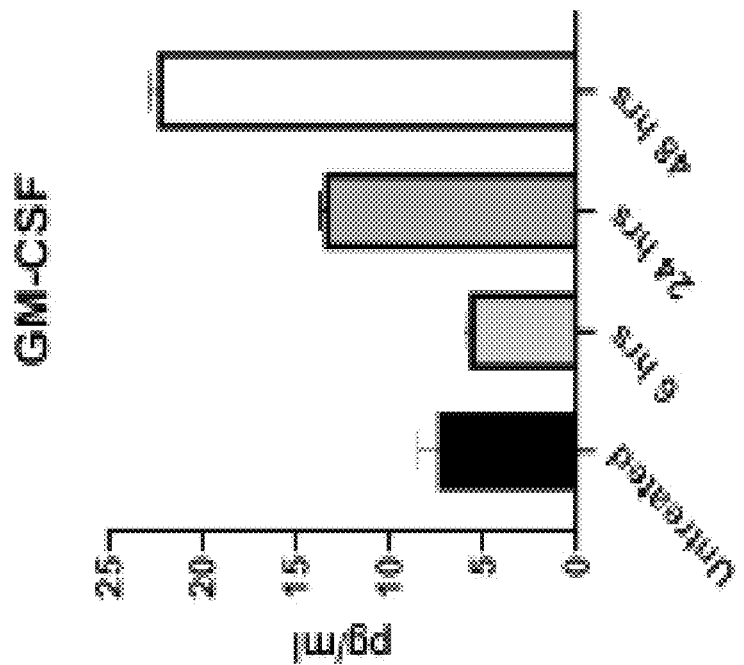
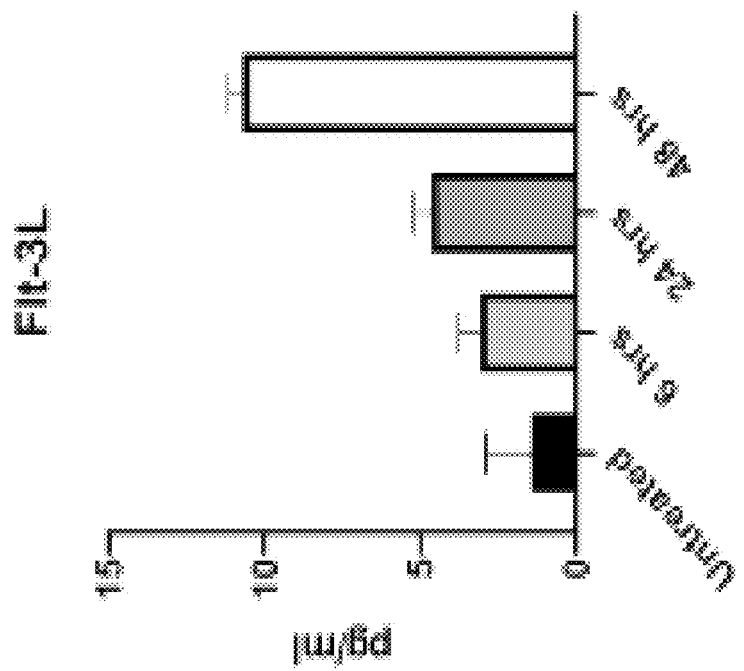

Fig. 9B

| RB | | | 1 μM | | 5 μM | | 20 μM | | 50 μM | |
|---|---|---|---|---|---|---|---|---|---|---|
| 0.15 μM Remdesivir | - | + | - | + | - | + | - | + | - | + |
| % Inhibition | 15.0 | 9.0 | 14.3 | 4.5 | 4.5 | 17.3 | 38.3 | 41.4 | 52.6 |
| SD | 9.1 | 8.5 | 13.7 | 12.8 | 18.8 | 7.9 | 4.7 | 8.1 | 2.3 |
| % Plaque Forming Unit | 85.0 | 91.0 | 85.7 | 95.5 | 95.5 | 82.7 | 61.7 | 58.6 | 47.4 |
| SD | 9.1 | 8.5 | 13.7 | 12.8 | 18.8 | 7.9 | 4.7 | 8.1 | 2.3 |

USES OF HALOGENATED XANTHENES IN ONCOLOGY AND VIROLOGY

FIELD OF THE INVENTION

The present invention relates to the therapeutic use of a halogenated xanthene molecule that exhibits therapeutic or immunotherapeutic properties in selected oncology and virology conditions.

BACKGROUND ART

Oncology and virology are tangentially related fields that intersect at the innate and adaptive immune systems of animals, in particular humans. Whereas disease etiology and manifestations are generally distinct, this intersection provides a common basis for the application of discoveries in one field to the other. Here, we synthesize novel approaches applicable to both fields by fusing new discoveries independently made in each field.

Coronaviruses (CoVs) are enveloped, positive-sense viruses containing a single-stranded ribonucleic acid RNA (ssRNA) genome. Discovered in the 1960s, they occur naturally in multiple mammalian and bird species. CoVs have posed a global health threat several times in recent decades upon crossover from native host species to humans (e.g., SARS-CoV in 2003, MERS-CoV in 2012, and now SARS-CoV-2, since late 2019). In humans they cause respiratory infections that can range from mild to fatal. The human diseases attributed to these CoVs are severe acute respiratory syndrome (SARS), Middle East respiratory syndrome (MERS), and CoV disease 2019 (COVID-19), respectively.

CoVs are pleomorphic spherical particles (approximately 12 nm diameter) with multiple bulbous surface projections (surface proteins that form spike-like peplomers). The viral envelope consists of a lipid bilayer anchoring these peplomers. Inside the envelope is a nucleocapsid that binds multiple copies of the viral RNA genome. Together, the envelope, membrane proteins and nucleocapsid protect the viral genome when outside of a host cell.

Infection begins when a peplomer attaches to a complementary host cell receptor on a tropic cell (a cell capable of supporting viral infection and growth) and virus or viral components enter the host organism. After attachment, a protease of the host cell cleaves and activates the receptor-attached peplomer. Depending on host cell protease availability, cleavage and activation permit cell entry through endocytosis or direct fusion of the viral envelop with the host membrane. Once inside the cell, the viral RNA is transcribed by ribosomes of the host cell, leading to replication of the virus. The resultant progeny CoV particles are released from the host cell by exocytosis.

Human infection is dependent on interaction of the CoV peplomers with a complementary host cell receptor. This determines tissue tropism and infectivity of a given virus.

Work reported by Zihe Rao and his co-workers noted the three-dimensional-shaped but not protein-sequenced similarity of the substrate binding site of the main protease) ($M^{pro}$) protein of the four virus groupings, I, II, III, and IV. [Yang et al., *PLoS Biology* 3(10): e324 (2005).] $M^{pro}$ plays a pivotal role in viral gene expression and replication through the proteolytic processing of replicase polyproteins, and is thus an attractive target for anti-CoV drug design [Zhang et al., Science 10.1126/science.abb3405 (Mar. 20, 2020).] The $M^{pro}$s showed comparatively high sequence similarities within each CoV group. $M^{pro}$ is a homodimer, one of whose first actions is to cleave a portion of the N-terminal portion of one of its own proteins.

The Rao group, using a computational modeling approach, also reported preparation and use of a peptido-mimetic conjugated carbonyl-containing Michael acceptor molecule referred to as N3 that covalently binds to a surface structure and inhibits the activity of representatives of the CoV groups at a point that is pivotal to viral replication and transcription. The suicide inhibitor sequence was based on that of P1-P4 of the N-terminal autoprocessing site of CoV TGEV $M^{pro}$ [Yang et al., *PLoS Biology* 3(10):e324 (2005).]

Three years later, the Rao group reported further studies using additional CoV strains and provided crystallographic evidence of the inhibitory effects of their former and improved inhibitors. One improved inhibitor (N27) replaced a valine residue with an isoleucine residue, whereas the other (H16) replaced the N3 isoleucine 2-butyl side chain with a t-butyl side chain. [Xue et al., *J Virol* 82(5):2515-2527 (2008).]

Rao and co-workers published non-peer-reviewed work regarding the $M^{pro}$ of the new SARS-CoV-2. [Jin et al., *BioRxiv* Feb. 5, 2020.] They provided crystallographic information of their inhibitor N3 covalently bound to the $M^{pro}$ binding pocket, and reported that N3 as well as other known compounds inhibited the $M^{pro}$ activity with $IC_{50}$ values of 0.67 to 21.4 µM.

Among those inhibitor compounds were disulfiram and carmofur that are U.S. Food and Drug Administration-approved drugs, whereas ebselen, shikonin, tideglusib, PX-12, and TDZD-8 are currently in clinical trials or undergoing preclinical studies. Ebselen has the strongest inhibition of $M^{pro}$ activity with an $IC_{50}$ of 0.67 µM. In a detergent-based assay, however, TDZD-8 was found to be an aggregate-based inhibitor that might not specifically inhibit $M^{pro}$, and was therefore not considered further.

Ebselen was found to only partially modify the $M^{pro}$ viral cysteine, whereas other inhibitors such as carmofur completely modified that cysteine. In view of ebselen's being the strongest inhibitor, the authors opined that that compound and others also inhibit MP r° through affinity (non-covalent means).

COVID-19 is a highly infectious disease resulting from infection with SARS-CoV-2 and is characterized by SARS. Common symptoms include fever, cough and shortness of breath. Although most cases appear to be asymptomatic or have mild symptoms, some progress to severe pneumonia, acute respiratory distress syndrome (ARDS), respiratory failure, septic shock, multi-organ failure, and death. The mortality rate has been estimated at approximately 1.8% in the U.S. [COVID-19 Dashboard by the Center for Systems Science and Engineering at Johns Hopkins University, 1:26 P.M., Mar. 22, 2021; coronavirus.jhu.edu/map] but is highly dependent on age: compared to a reference group age 5-17 years, the U.S. Centers for Disease Control and Prevention estimate the rate of death is 45 times higher in 30-39-year-olds and 7,900 times higher in 85+-year-olds. This suggests that, in addition to contribution from underlying morbidity, decreased immune system facility may be an important factor in severity.

The lungs are the organ most affected by SARS-CoV-2 because the virus accesses host cells via the receptor angiotensin-converting enzyme 2 (ACE2), which is most abundant in the type II alveolar cells of the lungs. The virus uses its peplomers (knob-like structures or spikes) to connect to ACE2 and enter the host cell.

The density of ACE2 in each tissue correlates with the severity of the disease in that tissue and some have suggested that decreasing ACE2 activity might be protective, although another view is that increasing ACE2 using Angiotensin II receptor blocker medications could be protective. As the alveolar disease progresses, acute respiratory distress syndrome (ARDS) and respiratory failure can develop. ACE2 is also common in cardiac cells and may be the path for acute cardiac injury.

Remdesivir was approved for treating COVID-19 patients requiring hospitalization in October of 2020. The commercially available remdesivir is named VEKLURY® for injection, or for intravenous use (VEKLURY® label). It is believed to be the only currently approved medication for inhibition of SARS-CoV-2 replication. Otherwise, patients are managed with supportive care (e.g., fluid and oxygen support if needed) and monitoring and supporting other affected vital organs. Several investigational COVID-19 treatments are undergoing preclinical and/or clinical study, including: lopinavir/ritonavir; nitazoxanide; chloroquine and hydroxychloroquine; and tocilizumab.

Recommended dosage of remdesivir in adults and pediatric patients 12 years of age and older and weighing at least 40 kilograms (kg) is a single loading dose of 200 mg on day 1 followed by once-daily maintenance doses of 100 mg from day 2 infused over 30 to 120 minutes. VEKLURY® is supplied as 100 mg lyophilized powder in vial that needs to be reconstituted with sterile water for injection prior to diluting in a 100 mL or 250 mL 0.9% sodium chloride infusion bag. VEKLURY® injection supplied as 100 mg/20 mL [5 mg/mL] solution in vial must be diluted in a 250 mL 0.9% sodium chloride infusion bag.

For patients not requiring invasive mechanical ventilation and/or extracorporeal membrane oxygenation (ECMO), the recommended total treatment duration is 5 days. If a patient does not demonstrate clinical improvement, treatment may be extended for up to 5 additional days for a total treatment duration of up to 10 days (VEKLURY® label).

Remdesivir was developed as an antiviral drug for Ebola and Marburg virus infections, and has been shown to have activity against ssRNA viruses. It is a prodrug that metabolizes to an active form, GS-441524, that interferes with the action of viral RNA-dependent RNA polymerase, decreasing viral RNA production. Upon diffusion into a cell, remdesivir is converted to GS-441524 monophosphate, which is phosphorylated to the active nucleotide triphosphate form of remdesivir (RTP). [Padhi et al., *bioRxiv*, p. 4, posted Jun. 29, 2020.] Remdesivir has a half-life of about 0.89 hours, whereas GS-441524 has a half-life of about 25 hours [Tempestilli et al., *J Antimicrob Chemother*, doi:10.1093/jac/dkaa239 (accepted May 14, 2020)].

A recent publication from the Gotte group at the University of Alberta and others [Tchesnokov et al., *J Biol Chem* 295 (47):16156-16165 (Nov. 20, 2020)] provides for a second mechanism of inhibition that is a template-dependent inhibition.

Lopinavir/ritonavir (LPV/r) is a combination of lopinavir and low-dose ritonavir that was developed for the treatment and prevention of human immunodeficiency virus infection/acquired immune deficiency syndrome (HIV/AIDS). Both drugs are antiretrovirals of the protease inhibitor class. A three-way exploratory randomized study of LPV/r vs. umifenovir (an indole derivative used for influenza that blocks contact between the virus and tropic cells to inhibit viral membrane fusion) vs. no antiviral medication, showed no difference in activity against SARS-COV-2. [Li et al., *medRxiv* Mar. 19, 2020.]

Nitazoxanide is a broad-spectrum antiparasitic and broad-spectrum antiviral drug. It is the prototype member of the thiazolides, a class of drugs that are synthetic nitrothiazolyl-salicylamide derivatives with antiparasitic and antiviral activity. It has shown some promise in clinical trials against influenza, chronic hepatitis B virus (HBV), and chronic hepatitis C virus (HCV); it is also being researched for treatment of rotavirus and norovirus gastroenteritis. Antiviral activity appears to be via selective blocking of host transcriptional factors, such as maturation of viral hemagglutinin, impairing hemagglutinin intracellular trafficking and insertion of the protein into the host plasma membrane.

Chloroquine phosphate is believed to have antiviral function via increasing endosomal pH values that can interfere with the virus-cell fusion process. It may also act as a zinc ionophore, thereby allowing extra-cellular zinc to enter inside the cell and inhibit viral RNA-dependent RNA polymerase.

Hydroxychloroquine increases lysosomal pH values in antigen-presenting cells. In inflammatory conditions, it blocks toll-like receptors (TLR) on plasmacytoid dendritic cells (PDCs), decreasing TLR signaling, reducing activation of dendritic cells (DCs), and decreasing the inflammatory process.

The World Health Organization (WHO) announced a large, global trial on Mar. 20, 2020 to assess whether (a) remdesivir, (b) chloroquine and hydroxychloroquine, (c) LPV/r, or (d) LPV/r with interferon beta (IFN-8) have utility for treatment of COVID-19. [Kupferschmidt and Cohen, *Science* Mar. 22, 2020.] In addition, four large randomized controlled trials (RCTs) were performed in record time in 2020 delivering reliable data: (1) the National Institutes of Health (NIH) RCT included 60 hospitals participating all over the world and showed the efficacy of remdesivir in reducing the recovery time in hospitalized adults with COVID-19 pneumonia; (2) three large RCTs already completed, for hydroxychloroquine, dexamethasone and lopinavir and ritonavir respectively. These trials were done under the umbrella of the 'Recovery' project, headed by the University of Oxford. The project includes 176 participating hospitals in the UK and was set up to verify the efficacy of some of the treatments used for COVID-19 [Ortolani et al., *Clin Mol Allergy* 18:17 (2020)].

These three 'Recovery' RCTs concluded definitely: (a) that treatment with hydroxychloroquine provides no benefits in patients hospitalized with COVID-19; (b) that treatment with dexamethasone reduced deaths by one-third in COVID-19 patients that were mechanically ventilated, and by one-fifth in patients receiving oxygen only; and (c) that the combination of lopinavir and ritonavir is not effective in reducing mortality in COVID-19 hospitalized patients [Ortolani et al., *Clin Mol Allergy* 18:17 (2020)].

Tocilizumab (also known as atlizumab) is an immunosuppressive humanized monoclonal antibody against the interleukin-6 receptor (IL-6R). IL-6 is a cytokine that can play a key role in immune response and is implicated in the pathogenesis of many diseases. Some medical communities have reported improvement in some patients with severe symptoms using tocilizumab to treat COVID-19 patients; however, no definitive data are currently available.

A recently posted preliminary study, Horby et al., *medRxiv*, Feb. 11, 2021, indicated that a patient study involving about 4000 hospitalized patients presenting with clinical evidence of progressive COVID-19 [defined as oxygen saturation <92% on room air or receiving oxygen therapy, and C reactive protein (CRP) 75 mg/L] showed that allocation to tocilizumab is associated with a 13% proportional reduction in 28-day mortality (death rate ratio 0.86, 95% CI 0.77-0.96, p=0.007). The reported data suggest that in COVID-19 patients that are hypoxic and have evidence of systematic inflammation, treatment with a combination of a systemic corticosteroid plus tocilizumab would be expected to reduce mortality by about one-third for patients receiving simple oxygen and nearly one-half for those receiving invasive mechanical ventilation.

Those results support the use of tocilizumab, but other IL-6 antagonists are available. Although the effects of another monoclonal antibody IL-6 antagonist, sarilumab, in which only 48 patients received sarilmab, were similar to those using tocilizumab, two further studies have been completed and reports have not yet been published.

These efforts to address viral infection or the effects of viral infection (whether from SARS-CoV-2 or another virus) highlight several of the strategies available:

Blocking viral attachment to the host cell;
Blocking release of viral genes and possibly enzymes into the host cell;
Blocking replication of viral components using host-cell machinery;
Blocking assembly of viral components into complete viral particles;
Blocking release of viral particles to infect new host cells; and
Blocking inflammatory reactions to viral infection.

Viral attachment to the Host Cell.

A virus must go through a sequence of steps to infiltrate a target cell, beginning with binding to a specific receptor site on the surface of the host cell. If binding occurs, viruses with a lipid envelope must also fuse their envelope with the target cell, or with a vesicle that transports them into the cell. Once inside the cell, the virus uncoats itself and releases its contents. This process can be inhibited in two ways:

1) Using agents that mimic the virus-associated protein (VAP) and bind to the cellular receptors on the host cell; and
2) Using agents that mimic the cellular receptor and bind to the VAP on the virus.

Release of Viral Genes and Possibly Enzymes into the Host Cell.

Inhibition of viral uncoating has proved useful against influenza and rhinovirus infections. Approaches include blocking a pocket on the surface of the virus that controls the uncoating process; this structure is conserved across a range of rhinoviruses (RVs) and enteroviruses (EVs).

Replication of Viral Components Using Host-cell Machinery.

Blocking reverse transcription of the viral genome can be achieved through deactivation of the synthesis of viral RNA or deoxyribonucleic acid (DNA). Blocking of integration of viral DNA into the host genome can be effective against DNA viruses. Blocking transcription factors crucial to initiation of RNA transcription can block replication of viral components. Additional functional targets for blocking the hijacking of host cell machinery by the virus include translation/antisense, translation/ribozymes, and protease inhibition.

Assembly of Viral Components into Complete Viral Particles.

Rifampicin is an antibiotic that has demonstrated some effectiveness against vaccinia virus. Whereas its primary mode of action is inhibition of RNA synthesis by certain RNA polymerases, against vaccinia it reversibly blocks cytoplasmic assembly of viral particles in infected cells. This function appears to be conferred by interference with the quaternary structure of key viral membrane components, inhibiting self-assembly into complete viral particles.

Release of Viral Particles to Infect New Host Cells.

Two drugs, zanamivir and oseltamivir, treat influenza by preventing the release of viral particles from infected cells by blocking neuraminidases, which are found on the surface of influenza viruses and appear to be conserved across a wide range of strains of influenza.

Inflammatory Reactions to Viral Infection.

Rampant viral infection of tropic host cells can elicit severe local or systemic inflammatory reactions due to release of inflammatory signaling components from infected cells (e.g., cytokines, chemokines, and damage-associated molecular patterns [DAMPS] implicated in innate immune response; and T cells and other functional components of an adaptive immune response), leading to local or systemic symptoms of the infection. Approaches that treat such disease manifestations, such as reducing severe pulmonary inflammatory response, can provide vital disease control until the patient can mount an appropriate antiviral response, either through antiviral drug therapy and/or an adaptive immune response.

Although there are a number of agents that may have merit for controlling viral disease, through prevention of viral infection of tropic cells or functional activity of virus within infected tropic cells, or through modulation of uncontrolled inflammatory response during viral infection, new options for antiviral agents are clearly needed. This urgent need is highlighted by the lack of satisfactory agents capable of controlling CoVs and mitigating the dramatic impact CoVs can have on global society, such as COVID-19.

Interferon

Interferons (IFNs) are a class of signaling proteins (i.e., cytokines) central to cellular defense against viruses, infectious microbes and tumor cells. [Andrea et al., *Eur J Paed Neurol* 6 Suppl A (6):A41-A46 (2002).] For example, a virus-infected cell releases IFNs, signaling nearby cells to heighten their antiviral defenses. Interferons were named for their ability to "interfere" with viral replication by protecting cells from virus infections. [Parkin et al., *Lancet* 357 (9270): 1777-1789 (2001).]

In addition to direct antiviral effects, IFNs serve to activate immune cells (e.g., natural killer cells and macrophages) and up-regulate antigen presentation by increasing expression of major histocompatibility complex (MHC) antigens. IFNs are classified into three groups:

Type I IFN, consisting of IFN-α, IFN-ε, IFN-κ, and IFN-ω, are produced in response to viruses and, upon binding to cellular receptors, inhibit replication of viral RNA and DNA; type I IFN has an analogous role in immune signaling in response to cancer;
Type II IFN (IFN-γ) is activated by interleukin-12 (IL-12) and released by cytotoxic T cells and T helper cells; and
Type III IFN is implicated in immune responses to some types of viral and fungal infections.

STING Activation and Immune Activation

The stimulator of interferon genes (STING), a transmembrane protein resident in the endoplasmic reticulum (ER), is an important regulator of innate immunity and was first reported by Ishikawa et al., *Nature* 455(7213):674-678 (2008). Those authors found that STING induces type I IFN and exerts a potent antiviral state upon expression, whereas loss of STING can render cells extremely susceptible to viral infection.

More specifically, STING is activated by binding to cyclic di-nucleotides such as cGMP-AMP (cGAMP), which is produced as an intracellular second messenger when cGAMP synthase recognizes cytosolic DNA. Upon binding to cGAMP, STING causes its dimerization and translocation from the ER to the Golgi apparatus. After relocation, STING recruits a serine/threonine kinase, TANK binding kinase 1 (TBK1), leading to the phosphorylation of interferon regulatory factor 3 [IRF3] and the up-regulation of type I IFN and IFN-stimulated genes, including IFN-β and CXCL10. [Motani et al., *J Biol Chem* 293(20):7717-7726 (2018).]

Ishikawa et al., *Nature* 461(8):788-793 (2009) showed that STING deficiency in mice produces lethal susceptibility to herpes simplex virus type 1 (HSV-1) infection due to the lack of a successful type I IFN response.

STING induces type I IFN production when cells are infected with intracellular pathogens, which protects infected cells and nearby cells from local infection by binding to the same cell that secretes it (i.e., autocrine signaling) and nearby cells (i.e., paracrine signaling). A Type I interferon (IFN-I) response can be critical for providing an efficient protection against viral infections.

IFN-I production is rapidly triggered by the recognition by host sensors of pathogen-associated molecular patterns (PAMPs), such as viral nucleic acids. IFN-I-induced signaling converges on transcription factors, which rapidly induces the expression of hundreds of genes called interferon-stimulated genes (ISGs) [reviewed in Schoggins, *Annu Rev Virol.* 6(1):567-584 (2019)]. This antiviral signaling cascade occurs in virtually all cell types exposed to IFN-I.

ISGs, along with other downstream molecules controlled by IFN-I (including proinflammatory cytokines), have diverse functions, ranging from direct inhibition of viral replication to the recruitment and activation of various immune cells. A robust, well-timed, and localized IFN-I response is thus usually needed as a first line of defense against viral infection because it promotes virus clearance, induces tissue repair, and triggers a prolonged adaptive immune response against viruses. Sa Ribero et al., *Plos Pathog* 16(7):e1008737 (Jul. 29, 2020).

Sun et al., *Proc Natl Acad Sci, USA*, 105(21):8653-8658 (2009) showed that dimerization of STING was critical to this innate immune system signaling. Abe et al., *Mol Cell* 50:5-15 (2013) showed that acute STING activation (via dimerization) was required for protective function whereas chronic activation can lead to counterproductive inflammatory response and autoimmune disease.

In some cases, STING acts as an intracellular sensor of foreign and endogenous DNA, such as that leaked from a host cell nucleus and infecting pathogens. Such endogenous DNA may be responsible for autoinflammatory diseases such as systemic lupus erythematosus (SLE) or Aicardi-Goutieres syndrome (AGS). [Barber, *Nat Rev Immunol* 15(12):760-770 (December 2015).] Interestingly, it appears that, as described by Abe et al., above, regarding antiviral activity, acute STING activation (via dimerization) is required for protective function whereas chronic activation can lead to immune down-regulation.

Barber, above, notes similar activity against retroviruses and replication of RNA viruses. Thus, expression and dimerization of STING play critical cellular defense roles against infection by all major viral classes.

In addition to its antiviral role, Barber, above, also describes a similar function against bacterial infection. In that review, Barber noted that their studies highlight the delicate equilibrium between an appropriate immune response and inflammation, a balance that may be exploited by microorganisms. Barber further noted that those findings may have important implications in the development of STING-targeting adjuvants and the design of vaccines intended to induce robust, long-lasting adaptive immune responses.

These observations indicate that acute activation of STING can be crucial for antimicrobial activity (i.e., antiviral, antibacterial, antifungal or antiparasitic).

Recent research has shown that STING homodimers complex with cytoplasmic polynucleotides, particularly viral-related single-stranded and double-stranded DNA (ssDNA and dsDNA) molecules. Such dimeric STING-containing complexes were found indispensable for HSV-1-mediated transcriptional activation of a wide array of innate immune and proinflammatory genes in addition to type I IFN. [Abe et al., *Mol Cell* 50:5-15 (2013).]

STING activation in certain cell types triggers cell death including apoptosis and necrosis. This effect could be critical for preventing unnecessary or excessive inflammatory events and maintaining host immune homeostasis. Besides canonical immune responses represented by IFN and tumor necrosis factor (TNF) production, STING signaling can also induce cell death events in a variety of cell types.

Currently, several STING agonists have been developed to treat refractory malignancies. See, for example, the use of linked amidobenzimidazole (ABZI)-based compounds in Ramanjulu et al., *Nature* 564:439-443 (Dec. 20/27 2018).

Sali et al., (*PLoS Pathog, pages* 1-30, Dec. 8, 2015) reported identification of a small molecule STING activator capable of activating the type I IFN response by way of the transcription factor IFN regulatory factor 3 (IRF3). That molecule, also referred to as G10, triggered IRF3/IFN-associated transcription in human fibroblasts.

Further examination of the cellular response to that molecule revealed expression of multiple IRF3-dependent antiviral effector genes as well as type I and type III IFN subtypes. This led to the establishment of a cellular state that prevented replication of emerging ssRNA alphavirus species including Chikungunya virus, Venezuelan Equine Encephalitis virus, and Sindbis virus. Those authors reported that the G10 molecule did not bind directly to STING, but acted as an indirect activator of human STING-dependent phenotypes.

Guo et al., [*Antimicrob Agents Chemother* 59(2):1273-1281 (2015)] reported that the synthetic small molecule, 5,6-dimethylxanthenone-4-acetic acid (DMXAA), activated a STING-dependent signaling pathway to induce a type I IFN-dominant cytokine response in mouse macrophages, which efficiently suppressed HBV replication in cultured murine hepatocytes and in the livers of mice by reducing the amount of cytoplasmic viral nucleocapsids. DMXAA had previously been identified as an agonist for murine STING. Human STING failed to bind to or signal in response to DMXAA. [Conlon et al., *J Immunol* 190:5216-5225 (2013).] The direct effect of STING in this cascade appears to be on dendritic cells (DCs), which serve as intermediaries between the innate and adaptive systems.

STING has been recognized as an activator of immune responses by TBK1/IRF3 and NF-KB pathways and subsequent IFN and TNF production. STING is suggested to play critical roles in host defense, autoimmune diseases, and tumor immunity through the induction of pro-inflammatory cytokines. The application of targeting the STING pathway for cancer immunotherapy has been also been examined. [Liu et al., *Mediat Inflamm* (2018) Article ID 1202797, (4 pages).]

Barber [*Nat Rev Immunol* 15(12):760-770 (December 2015)] reviewed the role of STING-dependent innate immune signaling that largely parallels that in virology.

STING activation leads to activation of type I IFN, which has a priming effect on the adaptive immune system (activation of tumor antigen-specific T cells though cross-presentation of tumor antigens by DCs). Abrogation of STING in mice abrogates T cell response to melanoma as well as the activity of immune checkpoint inhibitors, and as observed in virology, Barber notes that chronic STING activation can play a role in promoting tumorigenesis.

The author concluded by noting "it is becoming apparent that STING has a key role in facilitating anti-tumour immune responses. Furthermore, stimulating STING activity within the tumour microenvironment may comprise a new immunotherapeutic strategy to help treat malignant disease." [Barber, *Nat Rev Immunol* 15(12):768 (2015)]

Immune function increases rapidly during early childhood and remains consistent across adulthood until onset of advanced age, as described by Simon et al., *Proc R Soc B* 282:20143085 (2015). Those authors note that the immune system undergoes profound remodeling and decline as a person ages. This immune senescence predisposes older adults to higher risk of acute viral and bacterial infection.

Although there appears to be little direct data on changes in STING expression and activation over age, it is likely this tracks the same pattern of overall decline in innate immunity with onset of advanced age (i.e., 60 years or greater), especially given the central role of STING in mediating innate antiviral immunity. These authors note a parallel increase in incidence of cancers with age (i.e., median age of onset of approximately 70 years in industrialized countries) that may also be attributable to decline in STING expression and activation with increasing age.

Further, the consistent observations of productive outcome for acute STING activation and counterproductive outcome for chronic STING activation in infectious disease and oncology point to a central role for acute STING activation in the treatment of infectious disease and oncology.

Halogenated Xanthene (HX) Compounds

Our previous studies have identified halogenated xanthene (HX) compounds and particularly rose bengal [4,5,6,7-tetrachloro-2',4',5',7'-tetraiodofluorescein] (RB, sometimes referred to herein as PV-10, which is an injectable aqueous formulation of RB) as novel therapeutic agents with potent activity following intra-tumoral injection or topical application. Rose bengal is the prototypical member of the HX compound class of molecule described by Singer et al. in U.S. Pat. Nos. 8,530,675, 9,273,022, and 9,422,260.

These molecules have several medical uses, including as injectable oncology drugs as described by Eagle et al. in U.S. Pat. Nos. 9,107,887, 9,808,524 and 9,839,688 and as topical dermatology drugs as described by Dees et al. in U.S. Pat. No. 8,974,363. Although RB has shown promise as an immuno-activating therapy for cancer [Liu et al., *Oncotarget* 7:37893 (2015)] and as an immuno-modulating therapy for inflammatory dermatoses [Krueger et al., *Psoriasis from Gene to Clinic* 2018], these molecules have not had a proposed role in direct activation of innate immunity.

The newly found high affinity for binding to the $M^{pro}$ exploitable pocket of the SARS-CoV-2 virus discussed hereinafter in greater detail may result, in part, from the high affinity RB and other HX compounds have for biomolecules, and in particular glycoproteins. For example, there are a number of published reports describing the high level of binding of RB to rat and rabbit plasma proteins upon intravenous administration (IV) [Tsao et al., *Drug Metab Dispos*, 16(3):482-489 (1988); and Luxon et al., *J Pharmacol Exp Ther* 289(1):296-305 (1995)].

Using equilibrium dialysis, more than 99.8% of RB is bound in serum from rats lacking serum albumin, indicating that several proteins are involved. In normal rats, 75-80% of the RB was recovered from the albumin fraction and the remaining 20-25% in other protein fractions [Tsao et al. 1988, supra; and Meurman, *Acta medica Scan, Supp* 167, Chapters I, III, V, VII, X and XII (1960)]. We have confirmed that RB exhibits a high degree of plasma protein binding in rat plasma using the ultracentrifugation method, with 99.0% plasma protein binding observed at 1 µM and 99.2% at 10 PM; and that this affinity is higher in human plasma, with 99.8% to 99.9% plasma protein binding observed at 1 µM to 10 µM, respectively.

This affinity for biomolecules, in particular glycoproteins, appears to be the result of the unique physico-chemical properties of the HX compounds, which are amphipathic. For example, RB has a solubility of at least 10% (100 mg/mL) in water, 3% (30 mg/mL) in ethanol and 6% (60 mg/mL) in 2-methoxyethanol [Floyd J. Green, *Sigma-Aldrich Handbook of Stains, Dyes and Indicators*, Aldrich Chemical Company, Inc., Milwaukee, WI, pages 637-638 (1990)].

When administered via intravenous methods (IV) to humans, the HX compounds are excreted via the bile without metabolism with a circulatory half-life of approximately 30 minutes; this led to historic use as an IV diagnostic of hepatic function. Starting with initial clinical demonstration by Delprat et al., *Arch Intern Med* 34:533-541 (1924), intravenous RB became routinely used as a diagnostic for hepatic impairment based on differential excretion. Introduction of 131I radiolabeled RB in the 1950s expanded use as an imaging agent [Taplin et al., *J Lab Clin Med* 45(5): 665-678 (1955)] that allowed direct imaging of the liver via gamma ray detection. In clinical use, radio-iodinated RB was often diluted with non-radiolabeled RB. The approved indication in the U.S. was for use as a diagnostic aid in determining liver dysfunction and for liver imaging at doses of up to 25 µCi of $^{131}$I RB (approximately 12 mg of RB) together with a blocking dose of non-radiolabeled RB (100 mg given 10 minutes prior to radiolabeled product dosing) to retard the excretion rate of the radiolabeled product to permit more time for liver scanning. We have repeated this procedure with non-radiolabeled RB to confirm the safety and pharmacokinetic properties of systemically administered RB using modern clinical tools and standards.

Yoshimoto et al., *J Food Hyg Soc Japan*, 25(4):352-355 (1984) reported studies of the effects of rose bengal orally administered to young male Wistar rats at 300 mg/kg/day dissolved in distilled water. Those workers reported no influence on growth rate, but RB caused a significant decrease in relative liver weight. No effect on $H^3$-UTP incorporation into RNA or RNA content in liver nuclei was noted. Similar concentrations of Ponceau 3R or Amaranth were reported to stimulate RNA synthesis in vivo.

SUMMARY OF THE INVENTION

The present invention contemplates several concepts related to the medicinal use of a halogenated xanthene (HX) compound, its pharmaceutically acceptable salts, an amide whose nitrogen atom is unsubstituted, substituted with one or two $C_1$-$C_4$ alkyl groups that are the same or different or together with the amido nitrogen atom form a 5- or 6-membered ring, a $C_1$-$C_4$ alkyl ester, an aromatic derivative (amide or ester) thereof, wherein the aromatic derivative is an ester or amide formed from an alcohol or monosubstituted amine having a 5- or 6-membered aromatic ring, or a 5,6- or 6,6-fused aromatic ring system that contains 0, 1 or 2 hetero ring atoms that are independently nitrogen, oxygen or sulfur. Rose bengal is a preferred HX compound and its disodium salt, rose bengal disodium, is the most preferred.

The invention more particularly contemplates the interaction of a halogenated xanthene (HX) compound, particularly rose bengal, in the processes of infection of a mammalian subject by viruses, bacteria, fungi and parasites, and SARS-family viruses, particularly infection by the coronavirus (SARS-CoV-2) that causes COVID-19, as well as induction of a type I interferon (IFN) immune response by STING, and an adjuvant, immunological, effect when administered systemically with other agents against cancerous tumors.

More particularly, one embodiment contemplates a method for treating a corona virus infection of a mammalian subject such as a human that comprises administering to that mammalian subject a corona virus-complexing (virus-binding) amount of a halogenated xanthene, a pharmaceutically acceptable salt, amide, ester, or aromatic amide or ester derivative discussed above. The corona virus particularly contemplated for treatment is that known as SARS-CoV-2, the causative agent of COVID-19 respiratory disease. The halogenated xanthene molecule utilized is preferably rose bengal disodium. It is also preferred that the administration be repeated one or more times.

In an allied aspect of this embodiment, the HX compound is administered in conjunction with a corona virus-complexing (virus-binding) amount of remdesivir. The two medicaments can be administered by infusion from a single aqueous pharmaceutical composition such as normal saline, or by separate aqueous pharmaceutical composition infusions, or one medicament, the halogenated xanthene, can be administered orally whereas the remdesivir is administered by infusion.

Another embodiment contemplates a method of inducing a type I interferon response in a mammalian subject, preferably a human, in recognized need of treatment such as one that presents with a microbial infection that comprises administering an amount of a halogenated xanthene, a pharmaceutically acceptable salt, amide, ester, or aromatic derivative discussed above, effective to induce that type I interferon response. The preferred halogenated xanthene is rose bengal disodium. When a $C_1$-$C_4$ alkyl ester halogenated xanthene is used, it is preferably a $C_2$ (ethyl) ester. When an aromatic derivative is used, it is preferably a benzyl, phenyl or a 2-, 3-, or 4-pyridyl (pyridyl) ester or amide, although other aromatic derivatives are also contemplated as is discussed hereinafter. The microbial infection can be a viral infection, an infection by a bacterium, a fungus or a single cell parasite such as that which is the causative agent of malaria, Plasmodium.

A method of enhancing a mammalian immunogen-specific immune response is also contemplated. That method comprises contacting mammalian cells present in a mammalian cell growth-supporting medium such as an in vitro culture plate or in vivo with a mammal's body, with an adjuvant-effective amount of a halogenated xanthene, a pharmaceutically acceptable salt, amide, ester, or aromatic derivative discussed previously, and an immunogen to which the immune response is to be enhanced.

This immunogenic-response is different from those obtained by intralesional injection of RB into a tumor, or the contacting of malignant hematologic cells with RB as shown in U.S. Pat. Nos. 7,648,695, 8,557,298 and 9,107,887, 10,130,658, U.S. Patent Publication 2019-0350893 A1, and the progeny of one or more thereof. The cancerous mammalian cells contacted in the above patents and application preferentially take up the RB which kills the cancer cells and causes the resulting ablated cellular debris to act as a self-vaccine to induce a distant immune response. In this immunogenic response, the HX compound such as RB acts to stimulate the STING response. Rose bengal disodium is the preferred HX compound.

Enhancement of the immune response can be determined by comparison of the appropriate immune molecules or cells such as cytokines, chemokines, antibodies, B cells and/or T cells by in vivo or in vitro techniques. Such comparisons can also be made by comparisons of tumor sizes, extent of viremia and the like that are usually utilized in this field.

Another embodiment contemplates a method of inducing a type I interferon response in a mammalian subject, preferably a human, that presents with a solid cancerous tumor or hematologic malignancy. Here, a contemplated method comprises systemically administering a halogenated xanthene, a pharmaceutically acceptable salt, amide, ester, or aromatic derivative discussed previously, that is effective to induce STING dimerization and thereby a type I interferon response in the mammalian subject. The amount of halogenated xanthene is less than the $IC_{50}$ for a cancerous tumor or hematologic malignancy present in the mammalian subject. The preferred halogenated xanthene is rose bengal disodium. When a $C_1$-$C_4$ alkyl ester halogenated xanthene is used, it is preferably a $C_2$ (ethyl) ester. When an aromatic derivative is used, it is preferably a benzyl, phenyl, 2-, 3-, or 4-pyridyl (pyridyl) ester or amide, although other aromatic derivatives are also contemplated as discussed above and more fully hereinafter.

A further embodiment contemplates a pharmaceutical composition that comprises both a corona virus-complexing amount of each of (a) remdesivir and (b) a halogenated xanthene (HX), a pharmaceutically acceptable salt, amide, ester, or aromatic derivative discussed above dissolved or dispersed in a physiologically acceptable aqueous carrier. The HX compound is preferably present in the pharmaceutical composition as a pharmaceutically acceptable salt, and that HX pharmaceutically acceptable salt is most preferably rose bengal disodium.

A method of treating a corona virus infection of a mammalian subject is also contemplated. In that aspect, a corona virus-complexing amount of each of remdesivir and a halogenated xanthene (HX) compound, a pharmaceutically acceptable salt, amide, ester, or aromatic derivative discussed above, is administered to said mammalian subject. Both medicaments can be administered parenterally as by infusion (IV administration). Such administration can be accomplished using a composition of the paragraph above, or the two medicaments can be separately infused. Alternatively, remdesivir can be administered parenterally and HX compound administered orally. Regardless of the means of delivery, the HX compound is preferably present as a pharmaceutically acceptable salt that is rose bengal disodium.

BRIEF DESCRIPTION OF THE DRAWINGS

In the drawings forming a portion of this disclosure FIG. 1B utilized a longer film exposure than FIG. 1A to highlight the presence of the STING dimer.

FIG. 3B shows a structural formula of rose bengal and residues of the spike protein (light gray) and the ACE2 protein (dark gray) that are identified by amino acid residue three-letter code and protein sequence position number;

FIGS. 4A and 4B are computer-prepared models in which FIG. 4A shows United Kingdom variant N501Y mutated SARS-CoV-2 viral spike protein (on the left side) and the human ACE2 protein (to the right side) using space-filling modeling for the proteins with a rose bengal (RB) molecule bound in a cleft between those two proteins, whereas FIG. 4B shows the same interaction using a ribbon model for the respective protein portions. The superimposed arrow points to the location of the N501Y in FIG. 4B;

FIGS. 5A and 5B are computer-prepared models of the interface between the complexed SARS-CoV-2 spike protein (on the left side) and the human ACE2 protein (to the right side) with a rose bengal (RB) molecule bound in a cleft between those two proteins, in which in which FIG. 5A shows South African variant N501Y- and K417N-mutated SARS-CoV-2 viral spike protein (left side) and human ACE2 (right side) using space-filling modeling, whereas FIG. 5B shows the same interaction using ribbon modeling for the respective protein portions. In FIG. 5B, the lower superimposed arrow points to the location of the N501Y mutation, whereas the upper arrow points to the location of the K417N mutation;

FIG. 9B is a table showing percent inhibition and percent plaque-forming unit compared to the DMSO-treated cells for each treatment (SD=standard deviation).

DETAILED DESCRIPTION OF PREFERRED EMBODIMENTS

Halogenated Xanthenes Bind Tightly to SARS-COV-2 $M^{pro}$

In addition to the direct implications for use of a HX compound in an immune adjuvant role, via the STING pathway as detailed hereinafter, we have investigated further potential use of HX compounds as a viral inhibitor. Jin et al. [*bioRxiv* Feb. 5, 2020 reported early results from an international, multidisciplinary effort to identify and screen potential antiviral agents against SARS-CoV-2, the causative agent of COVID-19 noted previously.

We used the SARS-CoV-2 drug target described by Jin et al. 2020 ($M^{pro}$) to model binding properties of RB on the SARS-CoV-2 $M^{pro}$ using AutoDock Vina and BIOVIA Discovery Studio platforms; this permitted us to model flexible ligand-receptor docking and determine overall binding energy based on inter-atomic distances. As controls for this modeling we used N3 and another antiviral candidate ("reference" molecule, one of 10,000 library molecules tested in the work by Jin et al. 2020 and shown to have nanomolar binding efficiency and broad-spectrum antiviral activity).

This literature from 2005, 2008 and February 2020 demonstrates that N3 and "reference" molecule, shown below, bind in the catalytic pocket of SARS-CoV-2

Reference Molecule

M$^{pro}$ and, upon binding, exhibit inhibitory activity against viral replication. Our modeling shows that RB exhibits stronger binding to the SARS-CoV-2 M$^{pro}$ than N3, indicating that it is a better antiviral candidate for SARS-CoV-2 than N3.

Figure 2A:
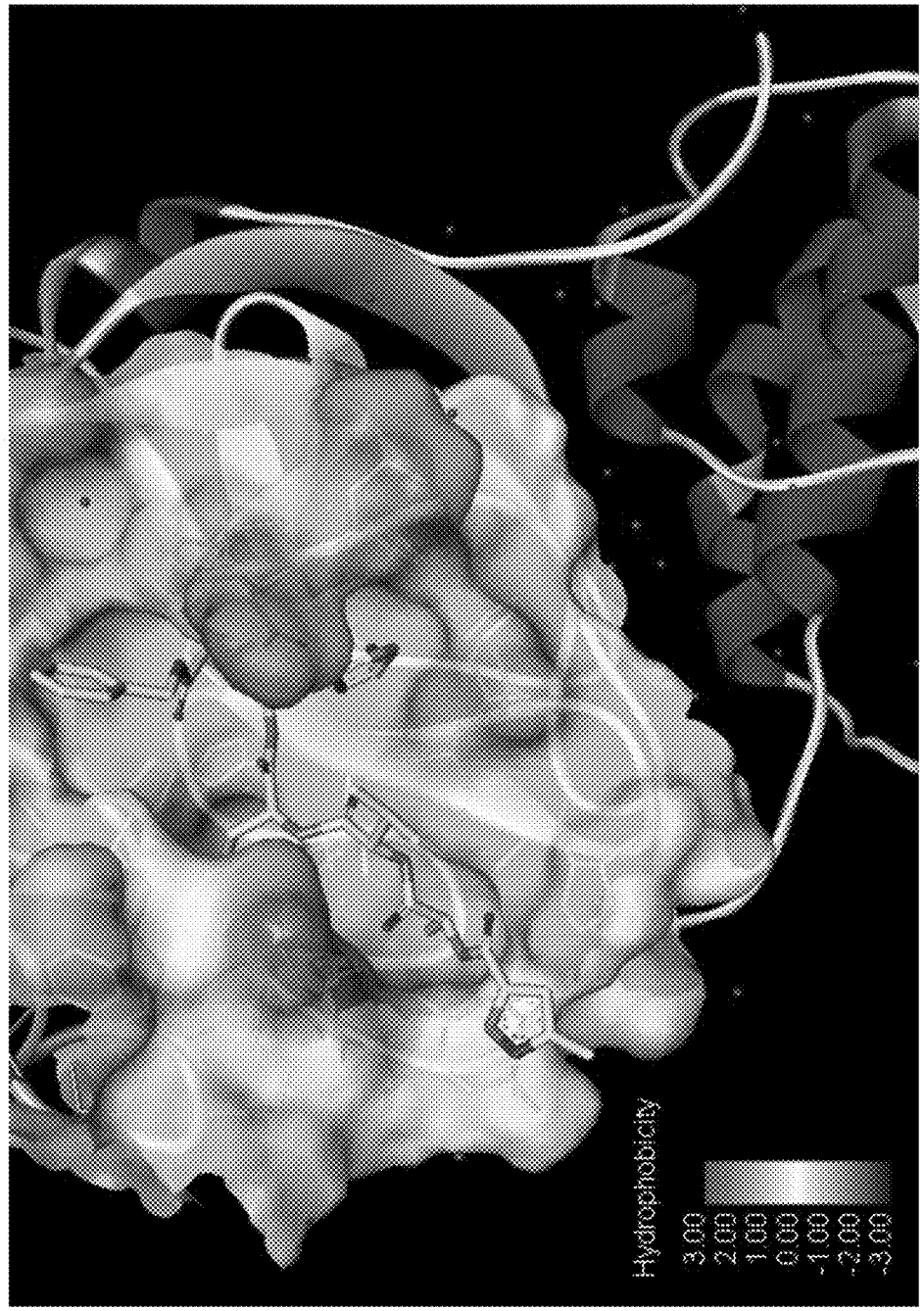
FIGS. 2A and 2B are computer-prepared models of SARS-CoV-2 main protease ($M^{pro}$) binding site (PDB: 6LU7) complexed with the N3 inhibitor (FIG. 2A) and "reference" compound (FIG. 2B) of Yang et al., *PLoS Biology* 3(10):e324 (2005).
Figure 2B:
Figure 2C:
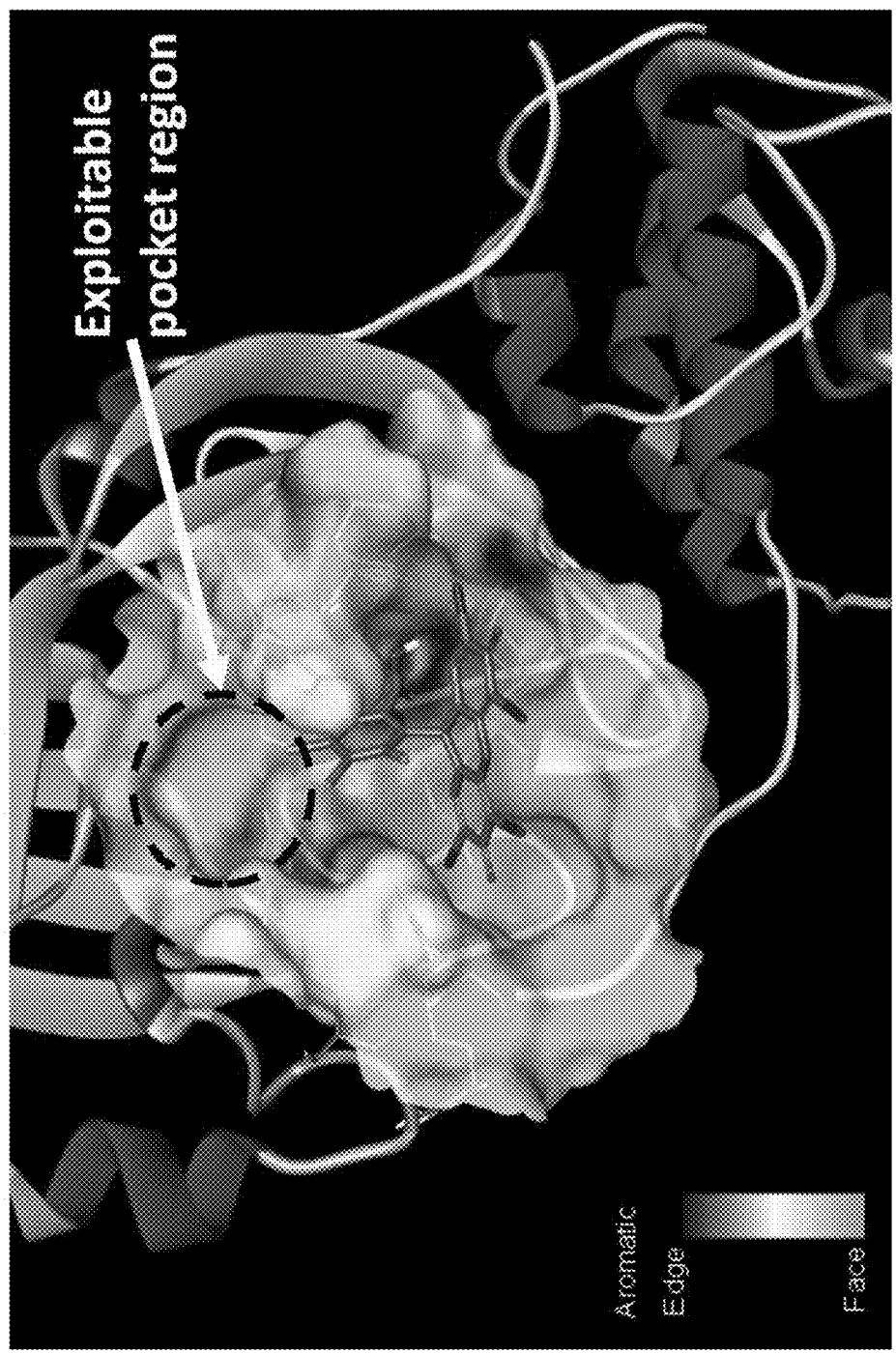
FIG. 2C shows a similar model having RB as an illustrative halogenated xanthene molecule complexed with the main protease ($M^{pro}$) binding site and further illustrates an exploitable pocket region that could accommodate a derivative of RB as discussed hereinafter. These models were prepared using the AutoDock Vina [Dr. Oleg Trott, Molecular Graphics Lab, Scripps Research Institute, LaJolla, CA] and BIOVIA Discovery Studio [*Dassault Systemes BIOVIA, Discovery Studio Modeling Environment, Release* 2017, San Diego, CA] platforms to perform in silico flexible ligand-receptor docking and determine overall binding energy based on inter-atomic distances.

These modeling results are illustrated in FIGS. 2A-2C, which represent the binding cavity of the SARS-CoV-2 main protease M$^{pro}$ complexed with N3 (FIG. 2A), with "reference" molecule (FIG. 2B) and with RB (FIG. 2C), respectively. Because the halogen composition of HX compounds can be varied, this fit can be optimized by varying halogen content (such as replacing one or more of the chlorine moieties at positions 4-, 5-, 6- or 7- with fluorine or bromine or a mixture thereof), and/or by replacing one or more of the iodine moieties at positions 2'-, 4'-, 5'- or 7'-with fluorine or bromine or a mixture thereof), or by aliphatic substitution at one or more of these positions.

Figure 3A:
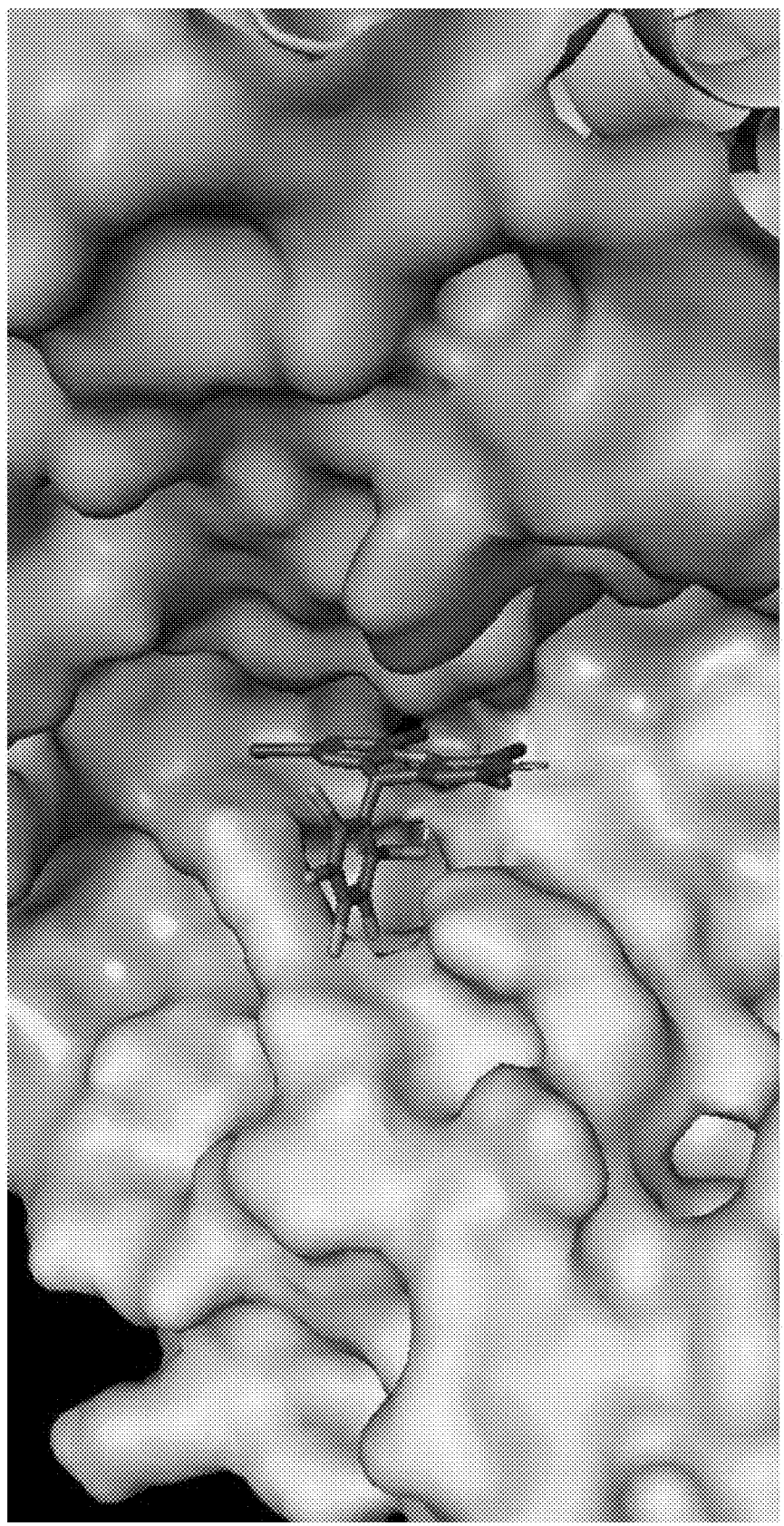
FIGS. 3A and 3B show the results from a computer-generated model of the interface between the complexed (docked) SARS-CoV-2 spike protein (on the left side) and the human ACE2 protein (to the right side) with a rose bengal (RB) molecule bound in a cleft between those two proteins in FIG. 3A.
Figure 3B:
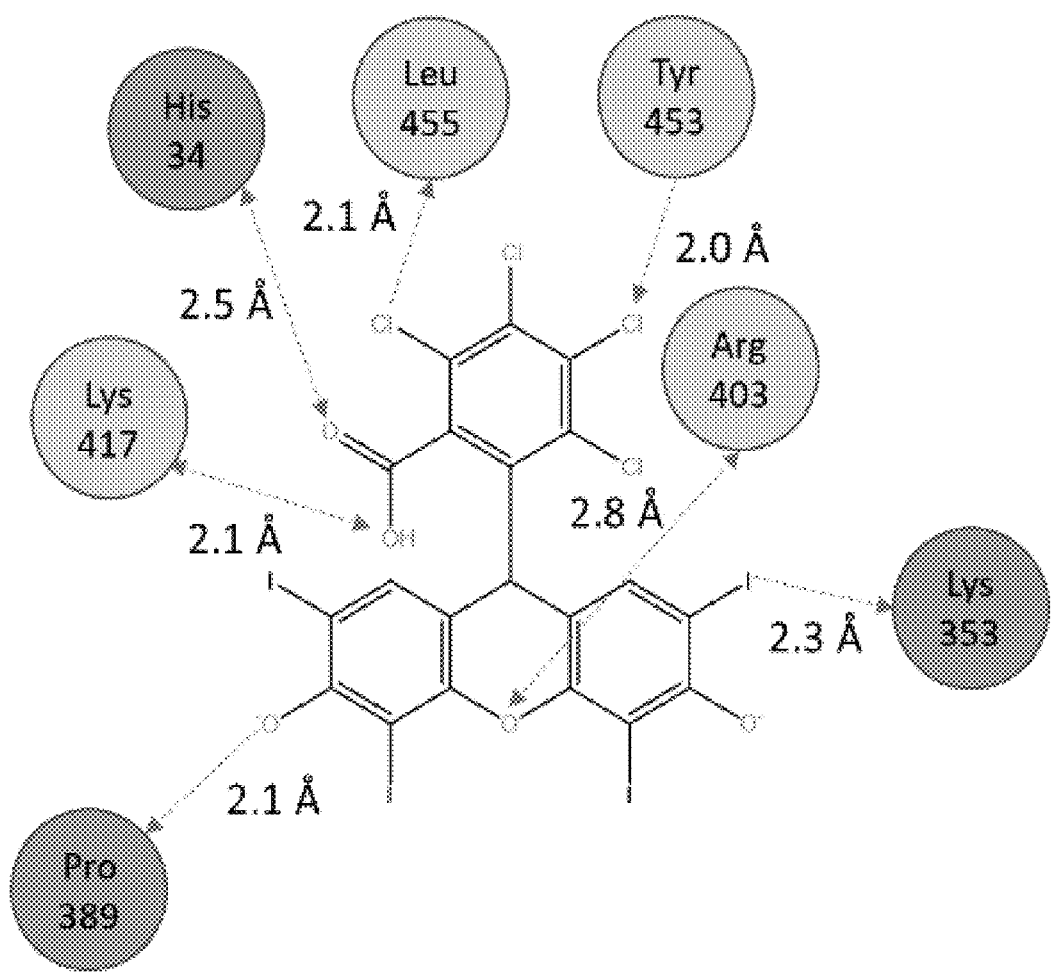

RB has been similarly computer-modeled bound to (complexed at) the interface of the SARS-COV-2 spike protein and its human cell surface binding partner, the human ACE2 protein (FIG. 3A). FIG. 3B shows the chemical formula for RB alone with the amino acid residues of the spike and human ACE2 proteins that interact with RB. RB was calculated to bind to (complex with) the non-mutated SARS-COV-2 spike and ACE2 protein pocket at about −12.5 kcal/mol.

Figure 4A:
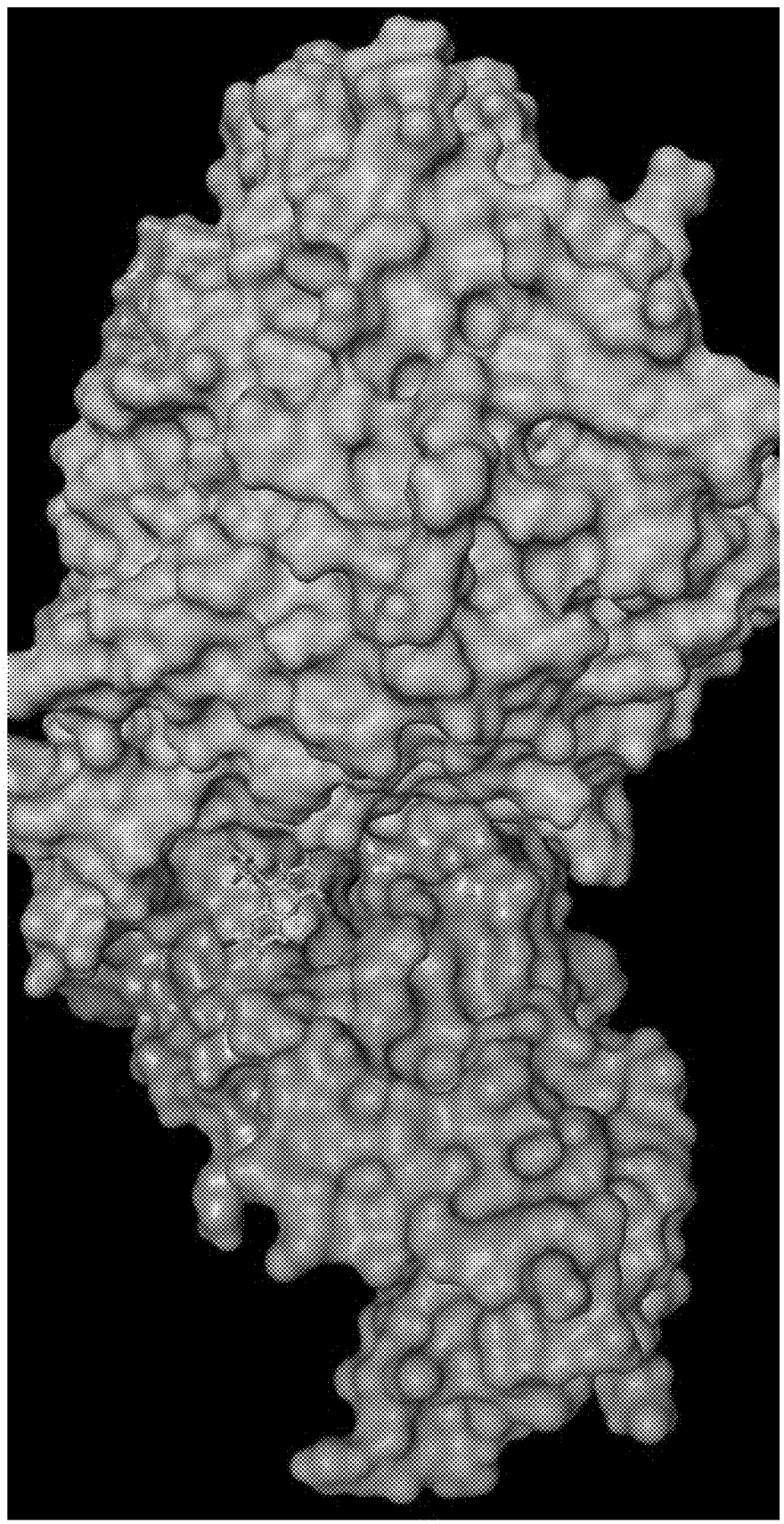
Figure 4B:
Figure 5A:
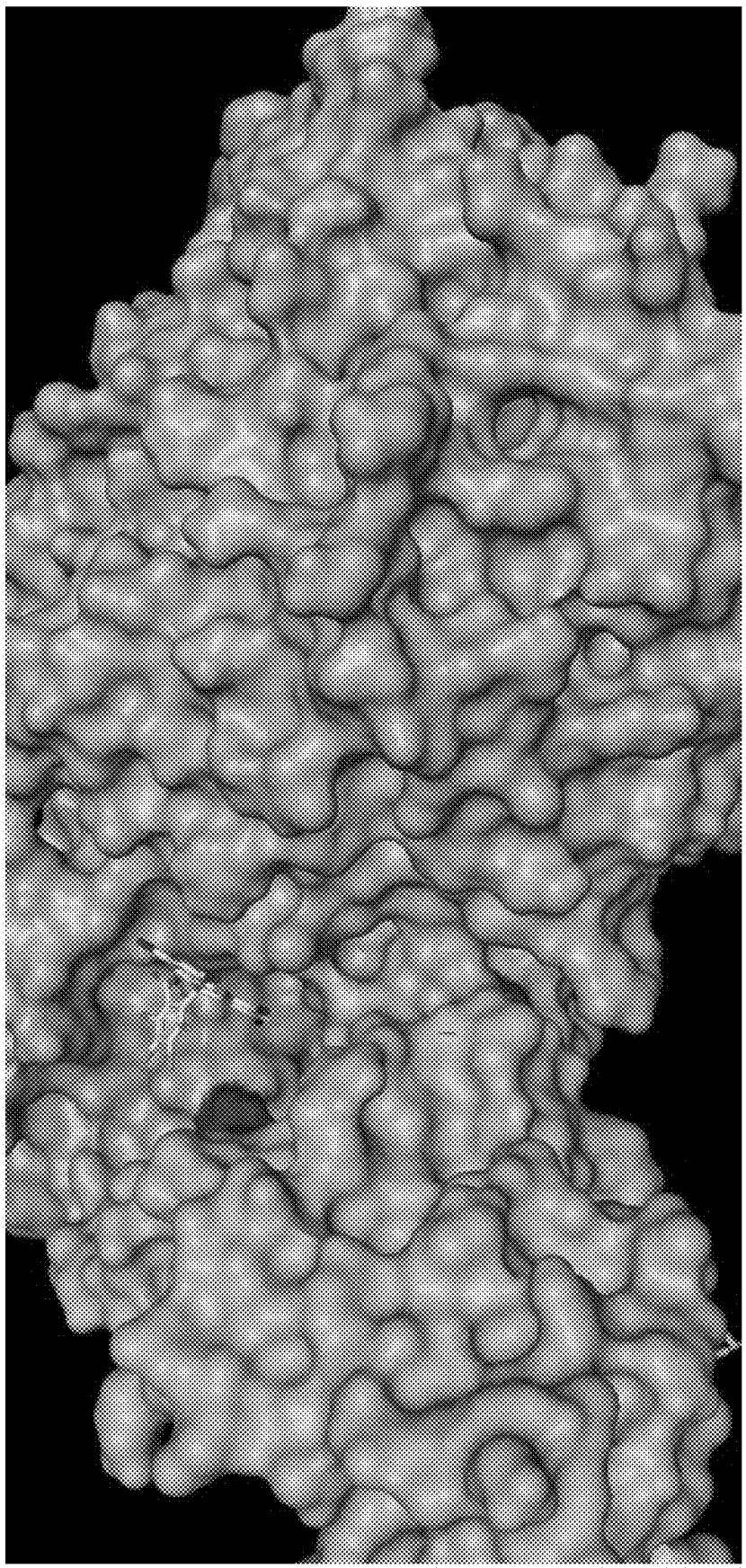
Figure 5B:

Similar binding efficiency using computer-modeling with the N501Y mutated SARS-COV-2 spike protein and ACE2 proteins showed about the same efficiency at about −13 kcal/mol. RB binds to the human ACE2-South Africa K417N mutated variant spike protein at about −17.5 kcal/mol. These computer models are illustrated in FIGS. 4A and 4B for the UK variant N501Y mutated SARS-COV-2 spike protein, and in FIGS. 5A and 5B using the South Africa variant N501Y and K417N mutated SARS-COV-2 spike protein.

A still further advantage of use of an HX compound such as RB as an antiviral agent against SARS-CoV-2 is that uncomplexed HX compound that is present in vivo can stimulate a type I interferon immune response in the treated subject via STING, and thereby obtain the advantage of an immune boost without the need of a separate medication. This feature is discussed in greater detail in the following paragraphs.

An alternate, common approach for combating viral infection is the use of a vaccine. These medicaments are traditionally predicated on exposing a patient's immune system to moderated or inactivated virus or viral antigens prior to exposure to live virus. This procedure allows the patient to develop an adaptive immune response capable of preventing significant infection of tropic tissues upon exposure to virus. Elucidation of the viral genome permits synthetic vaccine development to be undertaken based on modeling viral structure (i.e., surface proteins) to guide identification or synthesis of novel antiviral strategies [Graham et al., Ann Rev Med 70:91-104 (2019)]. Publication of the structure of the characteristic SARS-COV-2 surface spike (S) glycoprotein provides an important target for this type of focused development [Wrapp et al., Science 367: 1260-1263 (2020)].

In early 2020, the U.S. National Institutes of Health's (NIH's) National Institute of Allergy and Infectious Disease (NIAID) was funding development of a synthetic vaccine candidate produced using a messenger RNA platform to replicate these viral spike proteins (NIAID website, Jan. 31, 2020). This synthetic approach could elicit a functional immune response while avoiding exposure of patients to actual virus. An analogous approach was launched in early 2019 by the Coalition for Epidemiologic Preparedness (CEPI) to develop a "molecular clamp" vaccine platform, based on use of synthetic viral surface proteins to attach to host cells during infection and "clamp" them into shape; this could enhance immune system recognition (CEPI website, Jan. 23, 2020).

This unique CoV spike protein provides an alternate target for disabling viral function (i.e., preventing attachment to tropic cells or viral unpacking and replication) or as an immune adjuvant by increasing the antigenicity of virus to the host immune system. In particular, the extremely high affinity of RB and its HX compound analogs for glycoproteins conveys potential to: disable viral function by inhibiting attachment of CoV to tropic cells or by inhibiting viral unpacking and replication within infected cells; and as an immune adjuvant by increasing the antigenicity of virus to the host immune system upon complexation with CoV spike glycoprotein structures. Increased antigenicity can be used during early exposure to potentiate host immune response prior to onset of widespread infection.

Blocking function of viral activity via hinderance of host proteins in the viral interactome is another antiviral approach, and is the subject of an effort by Gordon et al. [bioRxiv Mar. 22, 2020] to evaluate interaction of potential small molecule drug candidates. Those authors noted their aim was to identify small molecules targeting human proteins in the SARS-CoV-2 interactome.

They sought ligands known to interact with the human proteins, often directly but also by pathway and complexes, drawing on chemoinformatics databases and analyses. Chemoinformatics searches of the literature yielded 15 approved drugs, four investigational new drugs (clinical), and 18 pre-clinical candidates, whereas specialist knowledge revealed 12 approved drugs, 10 investigational new drugs (clinical), and 10 pre-clinical candidates.

These efforts illustrate the value of structural-, functional- and genomic-guided drug design based on exploitable viral processes and structures.

The extremely high affinity of RB and its HX compound analogs for glycoproteins conveys potential to disable viral function by inhibiting interaction with host proteins critical to the viral interactome.

Rose Bengal-SARS-CoV-2 Complex Formation And Virus Titer/Viability Studies

In related aspect of this embodiment, Vero cells and the lung epithelial cell line Calu-3 (ATCC HTB-55) that was derived from a lung adenocarcinoma pleural effusion were used in these studies. Previous studies by Tseng et al., J Virol 79(15):9470-9479 (2005) have shown that a coronavirus (SARS-CoV) can productively infect Calu-3 cells, causing cytopathic effects, a process reflective of its natural course of infection in the lungs. These cells have been shown to express angiotensin-converting enzyme 2 (ACE-2), the functional receptor of SARS-CoV, on the apical surface and both ACE-2 and the virus co-localize at the apical domain of infected cells.

Figure 6A:
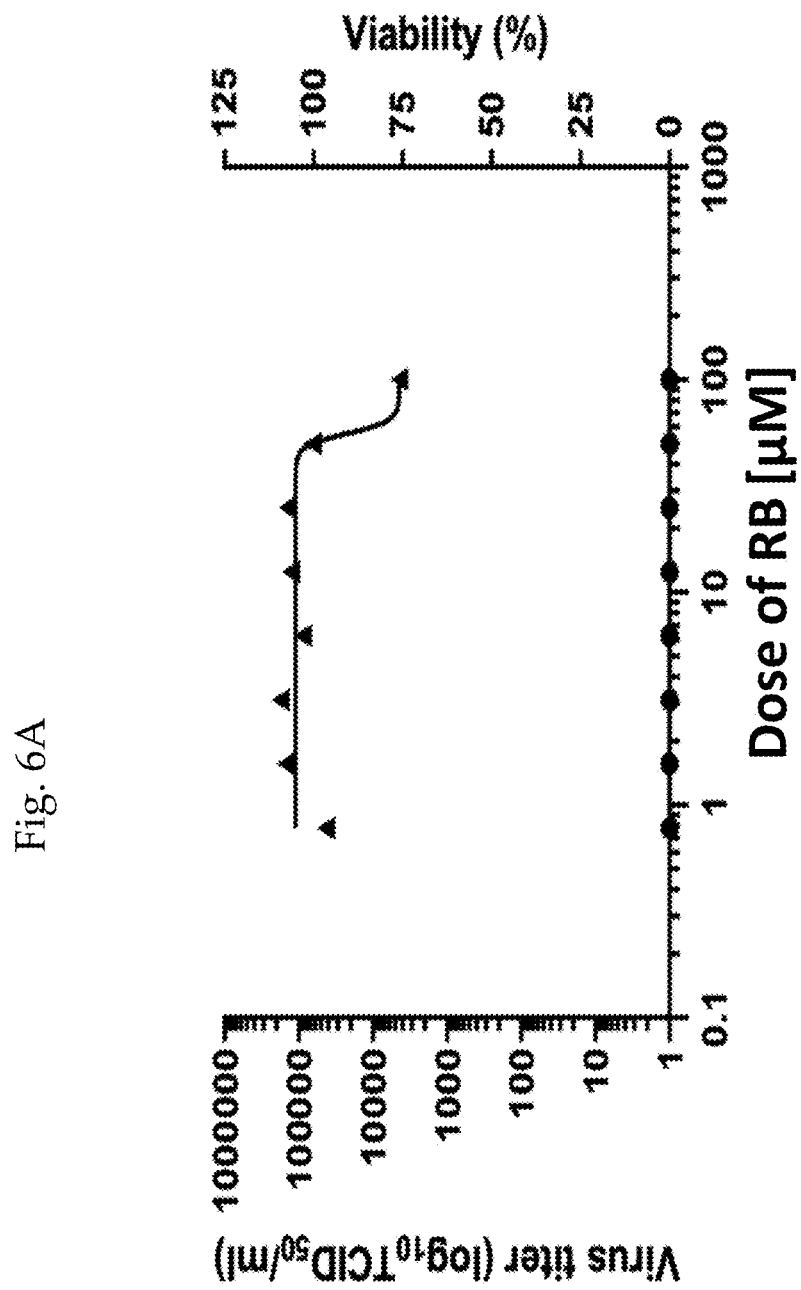
FIG. 6A is a graph showing SARS-CoV-2 viral-infected Vero cell viability (triangles) and virus titer (circles) as a function of concentration of RB in which complete inhibition of viral titers was seen and cell viability remained constant up to about a concentration of 50 μM.

Cells were treated with the virus concentrations as demonstrated to be optimal in previous studies with and without varying concentrations of rose bengal. In the first study, a concentration range of approximately 1 to 100 µM of rose bengal (RB) was studied for cell viability and viral titers in Vero cells after 48 hours of contact with RB. In this study, a complete inhibition in viral titers was seen and cell viability remained normal up to about 50 µM. This showed that RB was able to block viral replications at concentration that had no effect on cell viability (FIG. 6A).

Figure 6B:
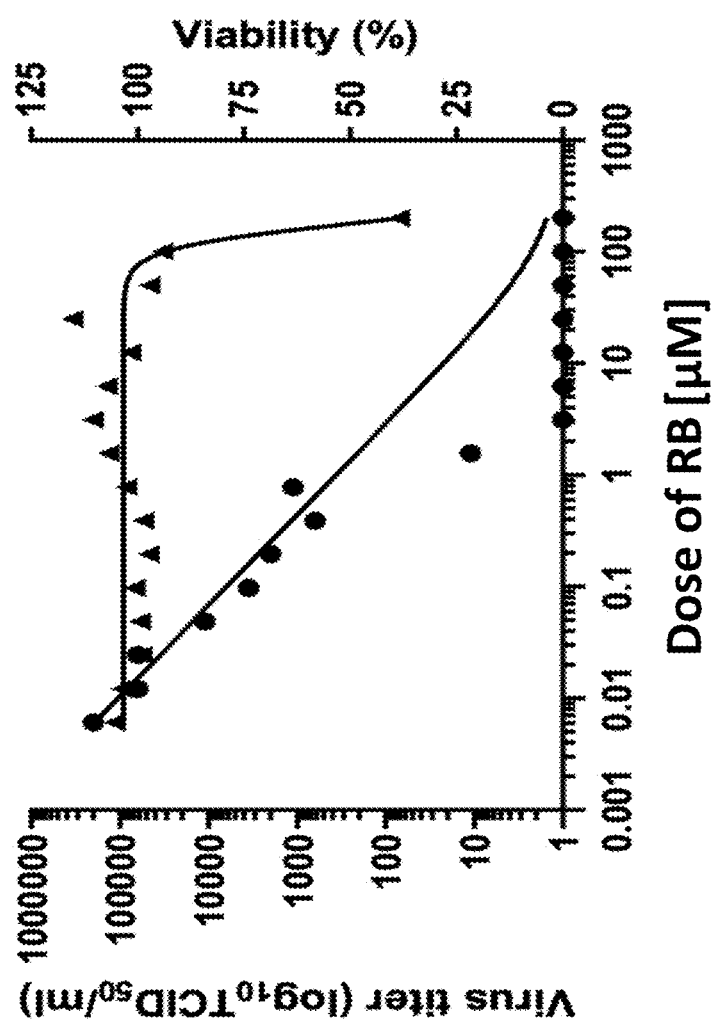
FIG. 6B is a similar graph over a wider concentration span of 0.01 to 100 μM.
Figure 6C:
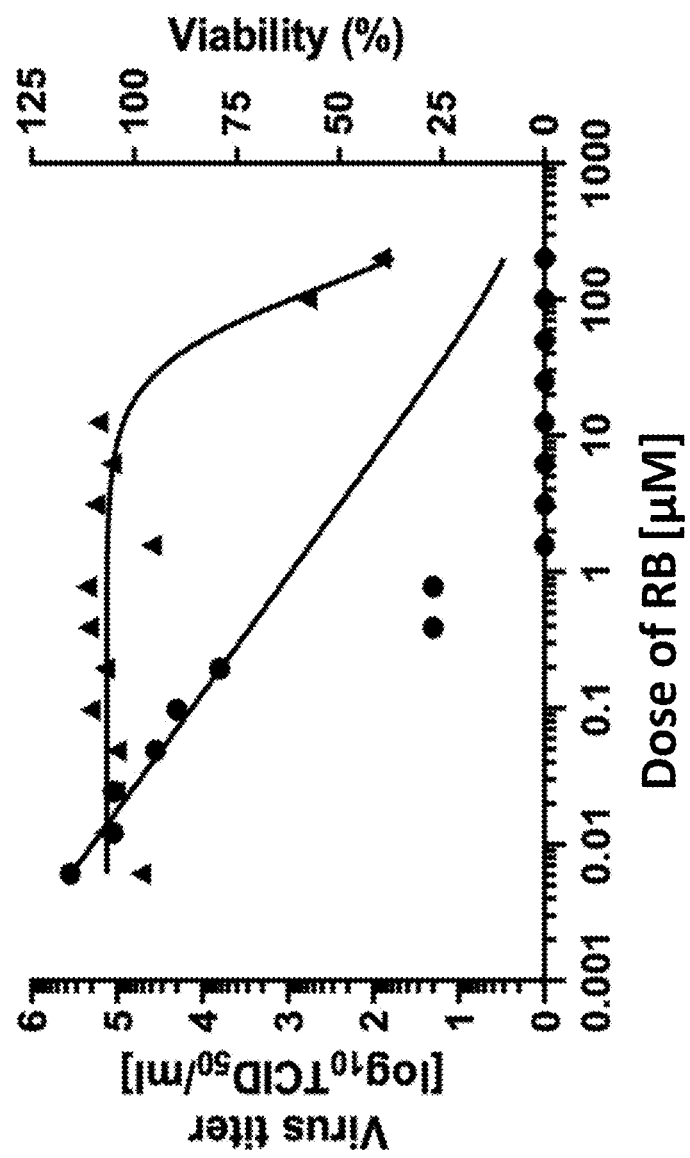
FIG. 6C shows data from repeated study over the RB concentration ranges shown in FIG. 6B.

The next study, also in Vero cells, included expanded lower concentrations to identify titration data. In this study, a dose-dependent decrease in viral titer was noted from 0.01 µM to about 100 mM RB contacted with the infected Vero cells for 48 hours at which concentrations no effect on cell viability was noted (FIGS. 6B and 6C). The inhibition values obtained after 48 hours were $EC_{50}$=0.054 µM, $CC_{50}$=174.8 µM and SI=3211. Similar findings were seen in 48-hour RB contact studies carried out in Calu-3 cells; ($EC_{50}$=0.015 µM). These findings indicated the ability of RB to achieve viral binding inhibition and subsequent replication in these cells.

Half maximal effective concentration ($EC_{50}$) refers to the concentration of a drug, antibody or toxicant that induces a response halfway between the baseline and maximum after a specified exposure time. The 50% cytotoxic concentration ($CC_{50}$) is defined as the compound's concentration (µg/mL) required for the reduction of cell viability by 50%. The selectivity index (SI=$CC_{50}/EC_{50}$ provides a measure of whether the compound has selectivity towards the virus or the host cells. The $EC_{50}$, $CC_{50}$ and SI values were calculated from data obtained 48 hours after addition of the RB.

Studies with Remdesivir

Figure 8A:
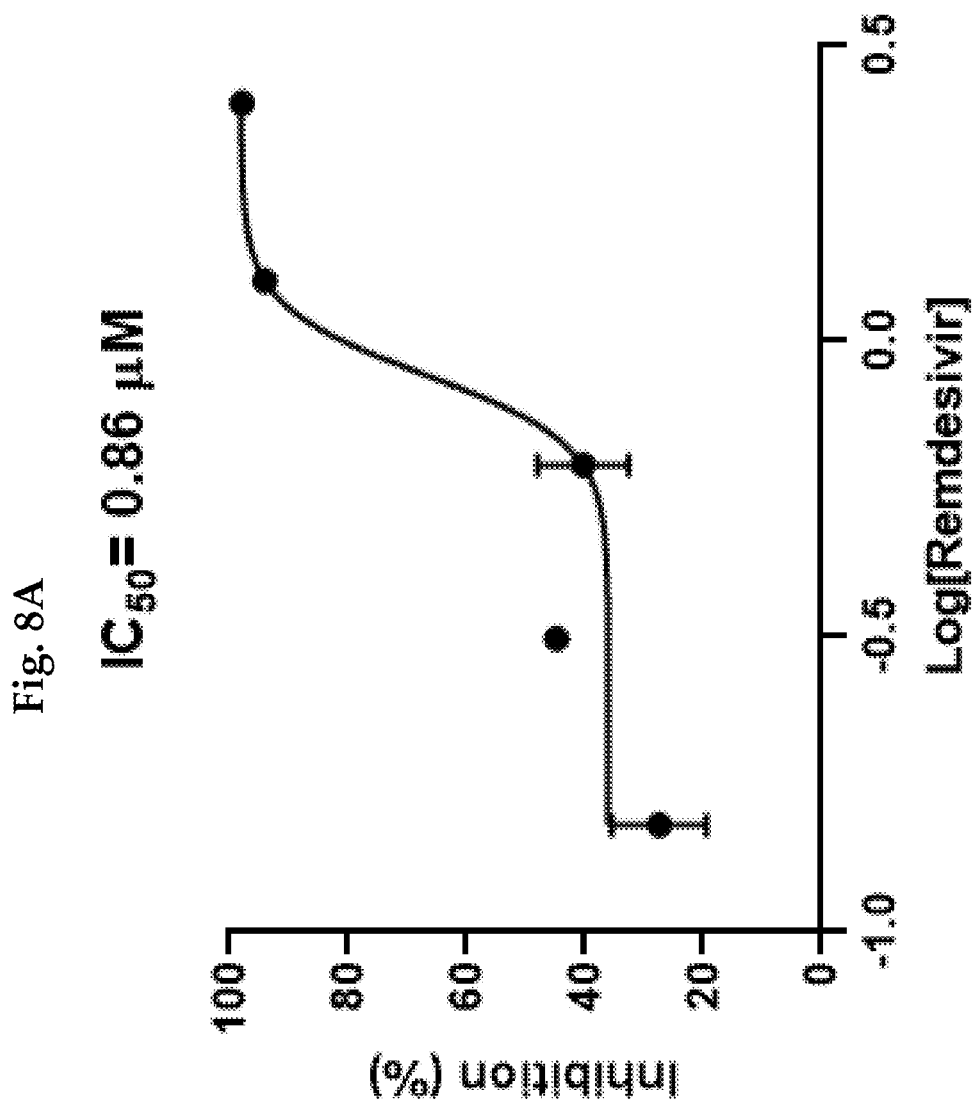
FIG. 8A is an inhibitory growth curve of SARS-CoV-2-infected cells as a function of concentration of Remdesivir. Percent inhibition was compared to DMSO-treated cells (±standard deviation).
Figure 8B:
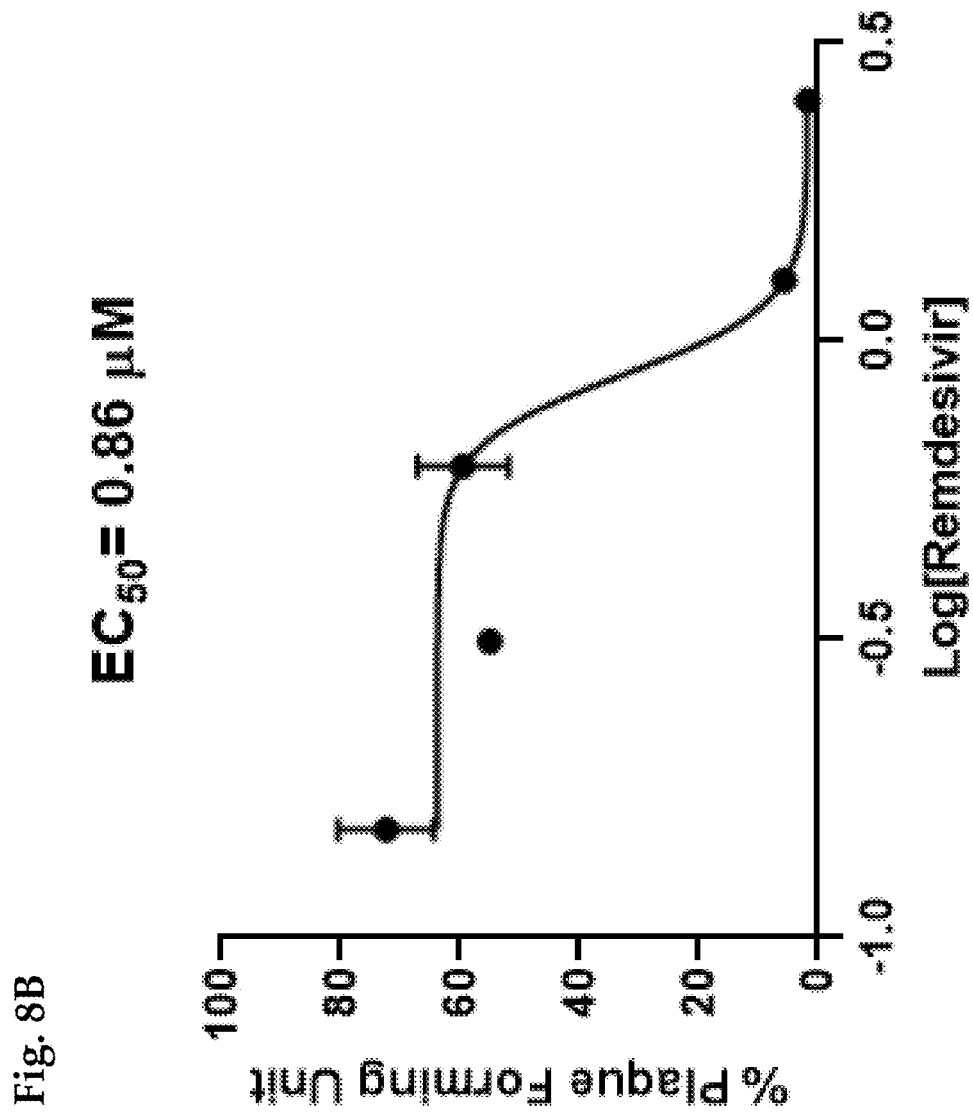
FIG. 8B is a curve similar to that of FIG. 8A illustrating percent plaque forming unit compared to DMSO-treated cells as a function of concentration of Remdesivir (±standard deviation).
Figure 8C:
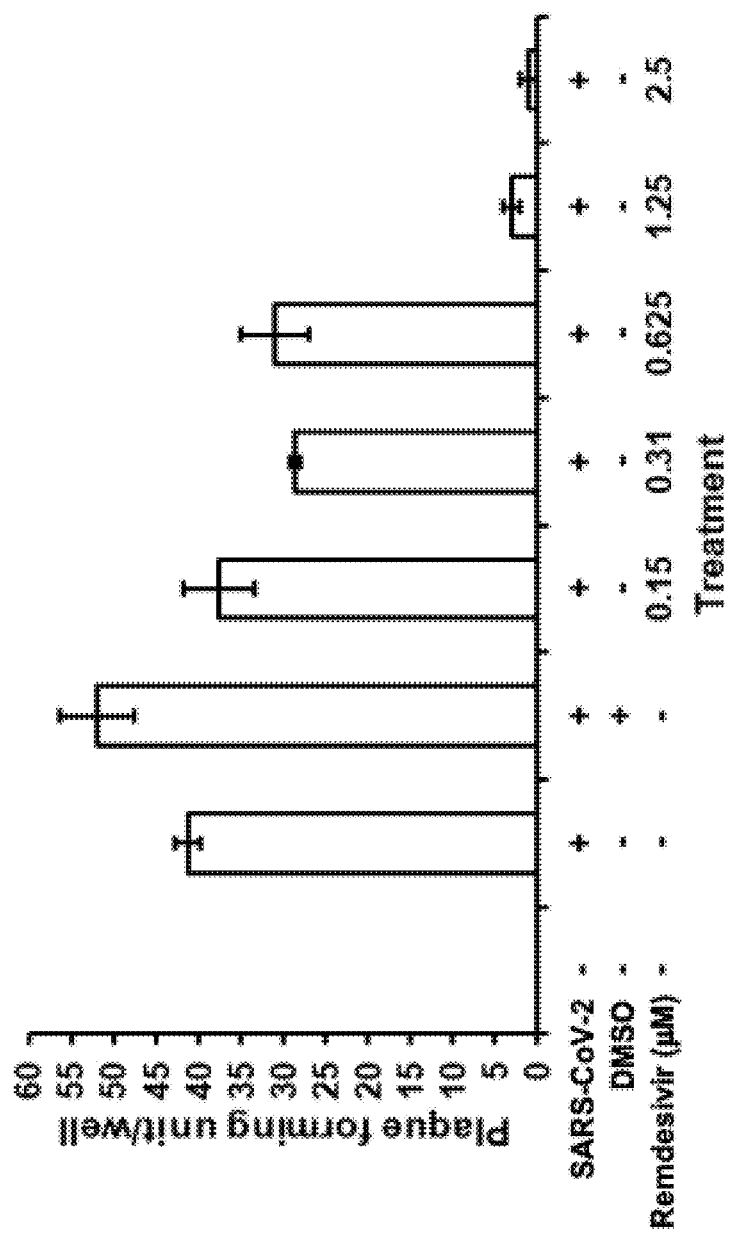
FIG. 8C is a bar graph showing quantification of infectious viral particles (plaque forming unit) in the presence of several concentrations of remdesivir (±standard deviation)

In a further aspect of this embodiment, SARS-CoV-2-infected Vero C1008 cells were shown to be susceptible to treatment with remdesivir as can be seen from the data in FIGS. 8A, 8B and 8C. $IC_{50}$ and $EC_{50}$ values of 0.86 µM for each were determined from the inhibition data measured 2 hours after addition of RB and remdesivir.

Figure 9A:
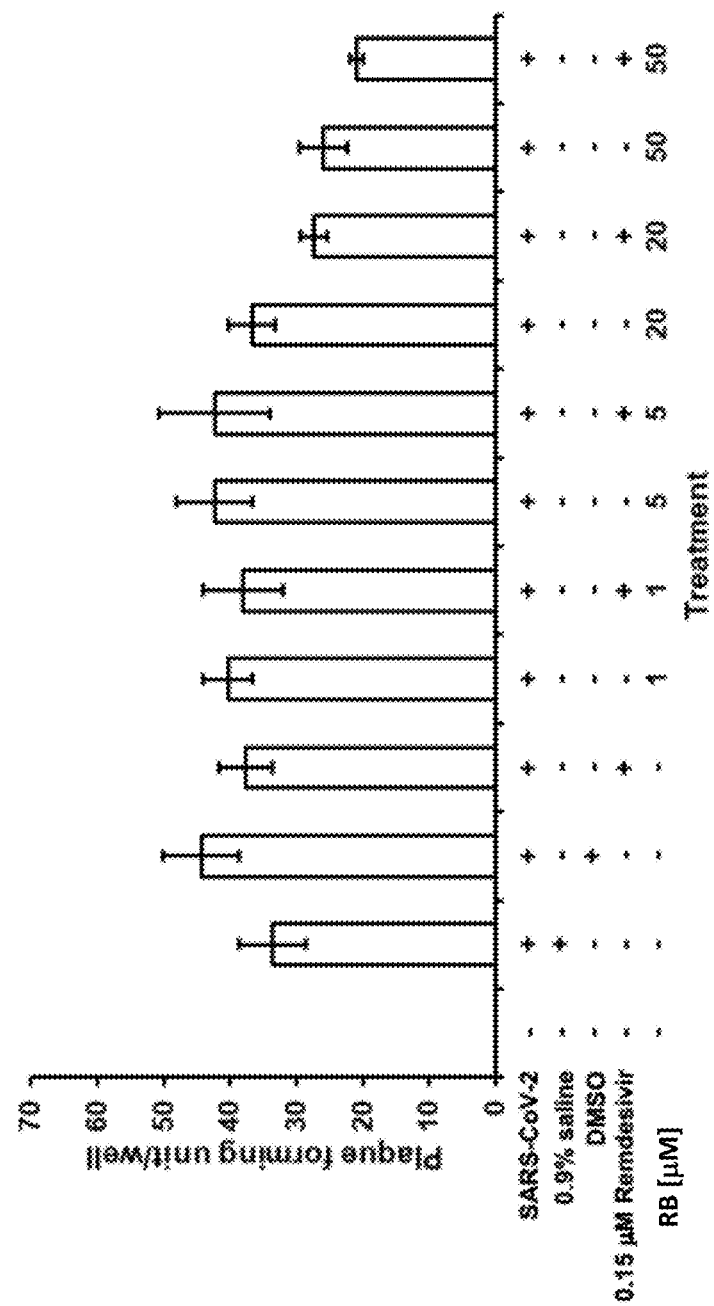
FIG. 9A is a bar graph showing plaque-forming units/well of titer plate in the presence or absence of 0.15 μM remdesivir and 1, 5, 20 or 50 μM RB (±standard deviation).
Figure 9C:
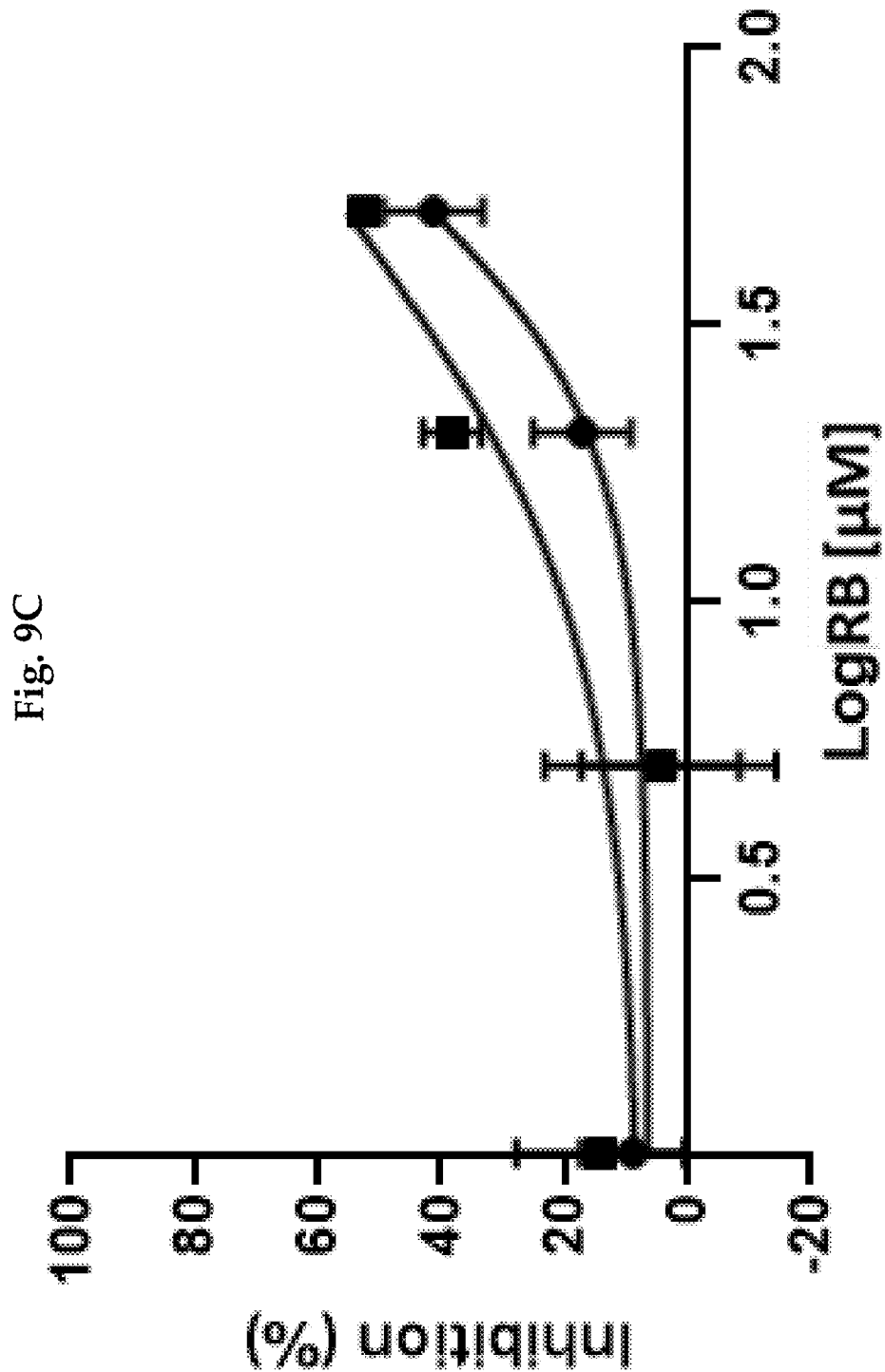
FIG. 9C is a graph showing growth inhibition of SARS-CoV-2-infected cells after 2 hours of contact with RB alone (circles), and the same 2-hour contact time with RB in combination with 0.15 μM remdesivir as a function of concentration of RB, from which their respective $IC_{50}$ values were calculated as RB alone=67.0 μM, whereas RB plus 0.15 μM remdesivir=47.4 μM.

SARS-CoV-2-infected Vero C1008 cells were also contacted with increasing concentrations of RB and a constant concentration of remdesivir (0.15 µM), and separately in the absence of remdesivir. The infected cells were found to be susceptible to RB alone and to a greater extent in the presence of both RB and remdesivir as can be seen from the data in FIGS. 9A, 9B and 9C. After contact with RB for 2 hours, the $IC_{50}$ value calculated for inhibition by RB alone was 67.0 µM, whereas the $IC_{50}$ value for RB plus 0.15 µM remdesivir after the same 2-hour contact time was 47.4 µM.

It thus appears that both remdesivir and RB have two separate mechanisms of inhibiting SARS-CoV-2 viral replication: remdesivir appears to directly inhibit the viral RNA-dependent RNA polymerase as well as the template strand, whereas RB appears to inhibit the main protease ($M^{pro}$) as well as the binding between the viral S protein and the human ACE2 protein largely responsible for viral entry into the cell that is infected. Interestingly, these four mechanisms are all different and orthogonal to each other so that they do not interfere with each other as can be seen by the fact that use of the two together reduced viral replication.

Remdesivir is typically administered parenterally, as by infusion. A contemplated HX compound, salt, amide or ester, as discussed more fully hereinafter is also preferably administered parenterally. Corona virus-binding amounts of each of those medicaments can be combined dissolved or dispersed in a single pharmaceutically (or physiologically) acceptable diluent to form a pharmaceutical composition. Each can also be administered parenterally as separate pharmaceutical compositions. Alternatively, remdesivir can be administered parenterally and the contemplated HX compound can be administered orally via separate pharmaceutical compositions.

Halogenated Xanthenes Activate STING

We have found that rose bengal (RB) is a promoter of STING dimerization and a resulting type I interferon response using a well-established acute monocytic leukemia (AML) cell line (THP-1) as a model to study STING activation in vitro. Cells were treated with RB and the induction of STING was evaluated by Western blot analysis using cyclic guanosine monophosphate-adenosine monophosphate (cGAMP) as a positive control.

These studies were carried out using RB at 100 µM, or about 0.01% RB. Cytokine assays were carried out prior to the addition of RB to the cell culture medium (0), and at 8, 24 and 48 hours thereafter.

Proteins that associate with STING in the presence of RB were purified by immunoprecipitation and analyzed by mass spectrometry (LC-MS/MS). The culture supernatants from RB-treated cells were probed for a panel of 42 immune cytokines using the Bio-Plex® multiplex bead-based assay system (Bio-Rad Laboratories, Inc.).

Figure 1A:
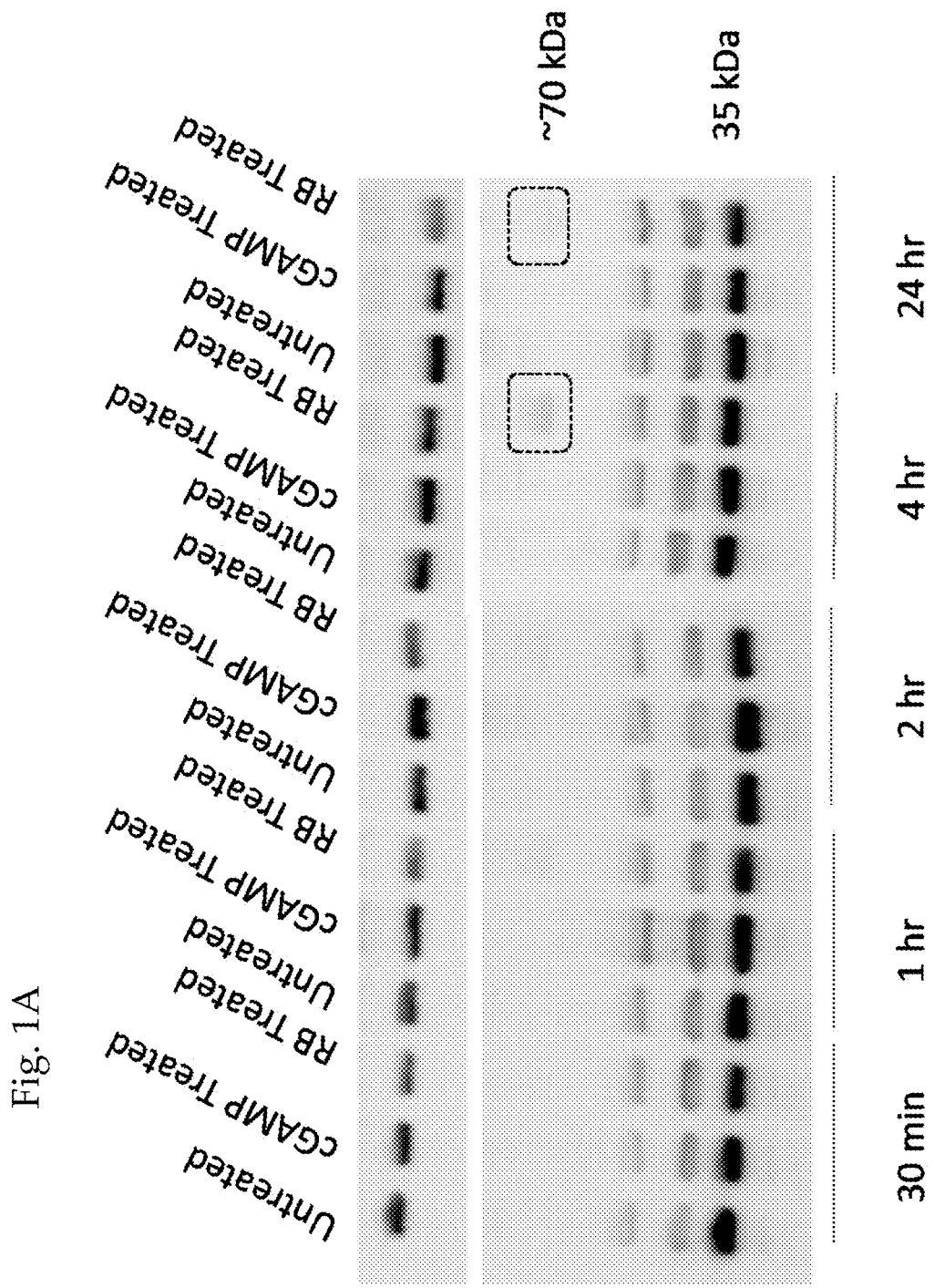
FIG. 1A and FIG. 1B are annotated photographs of Western blots from THP-1 acute monocytic leukemia (AML) cells contacted with RB for 30 minutes and 1, 2, 4 and 24 hours, and for 2, 4, 6 and 8 hours, respectively, that led to the appearance of a new 70-KD STING dimer band (dotted boxes) detected by specific antibodies.
Figure 1B:
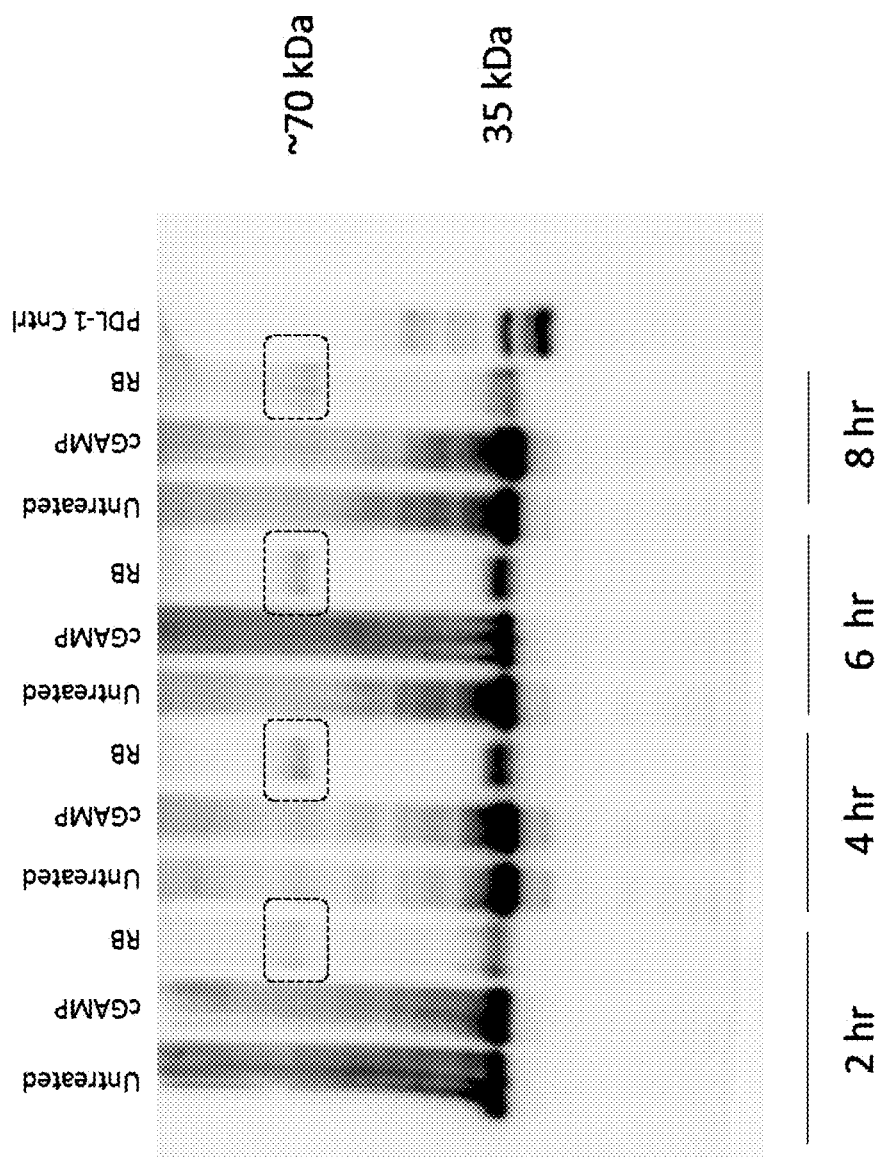
Figure 1D:
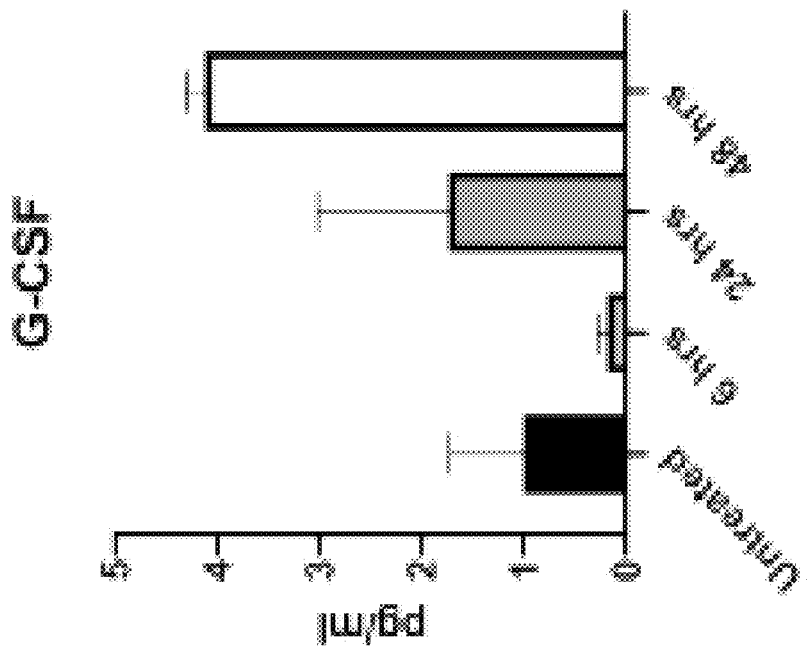
FIGS. 1C through 1R provide graphs of assayed amounts of the noted cytokines and chemokines from prior to RB contact with the THP-1 AML cells and at 6, 24 and 48 hours thereafter.

Exposure of THP-1 AML cells to RB led to the appearance of a new about 70-KD STING dimer band detected by specific antibodies FIGS. 1A and 1B (dashed boxes in the pictured gels). Compared to cGAMP controls, no induction of PDL-1 was noted. Mass spectrometric analysis of immuno-precipitates of STING in these cells showed the presence of heat shock proteins (HSPs) 60, 70 and 90 as well as polyadenylate binding protein 1 (PABP1) to the dimerized STING complex.

Figure 1C:
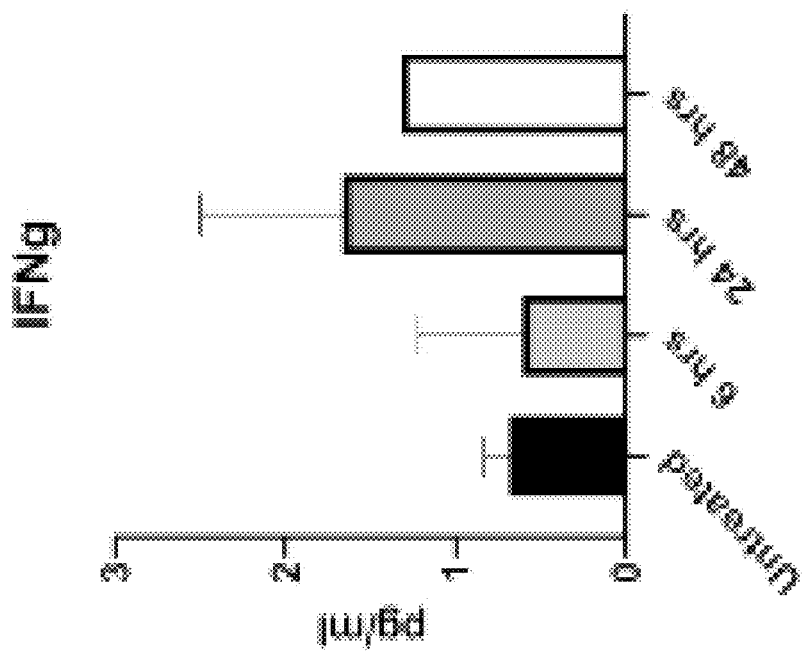
Figures 1G, 1H:
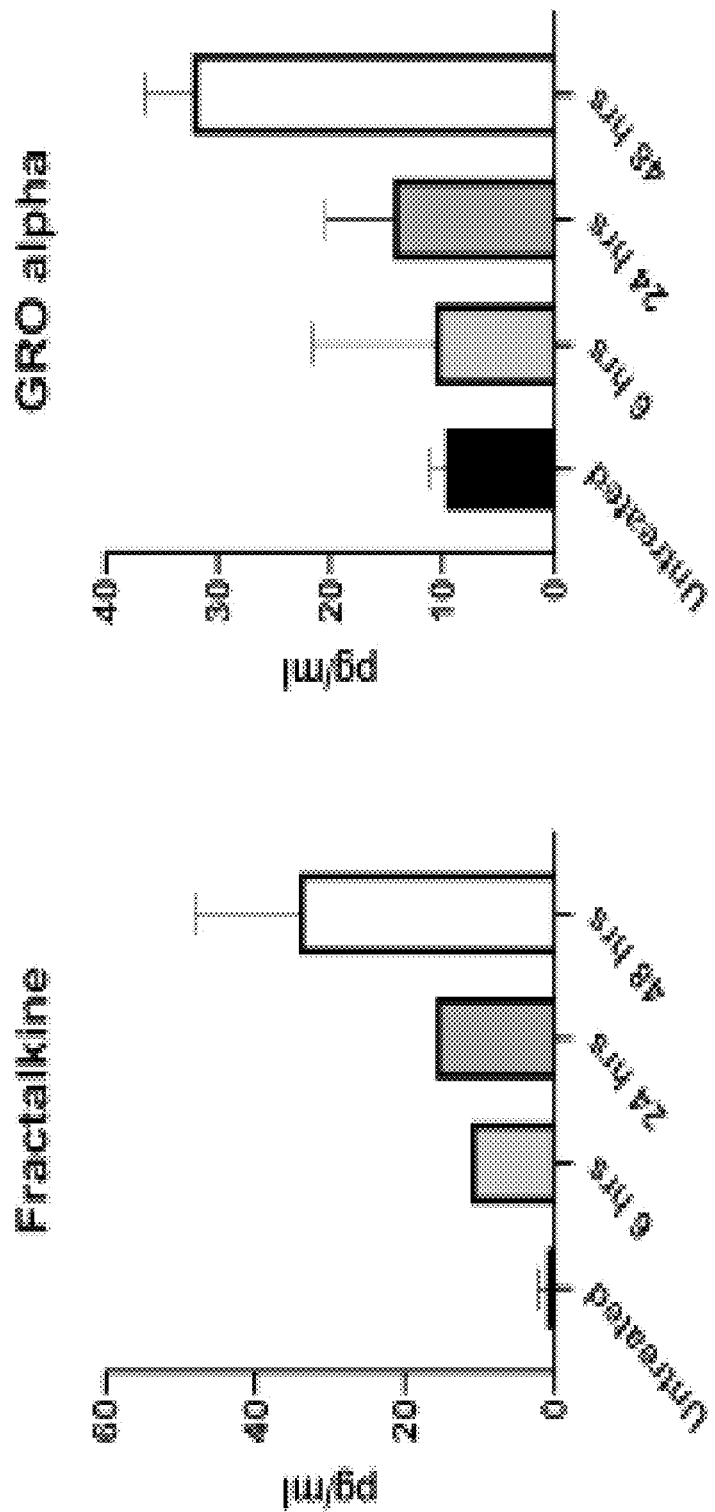
Figure 1J:
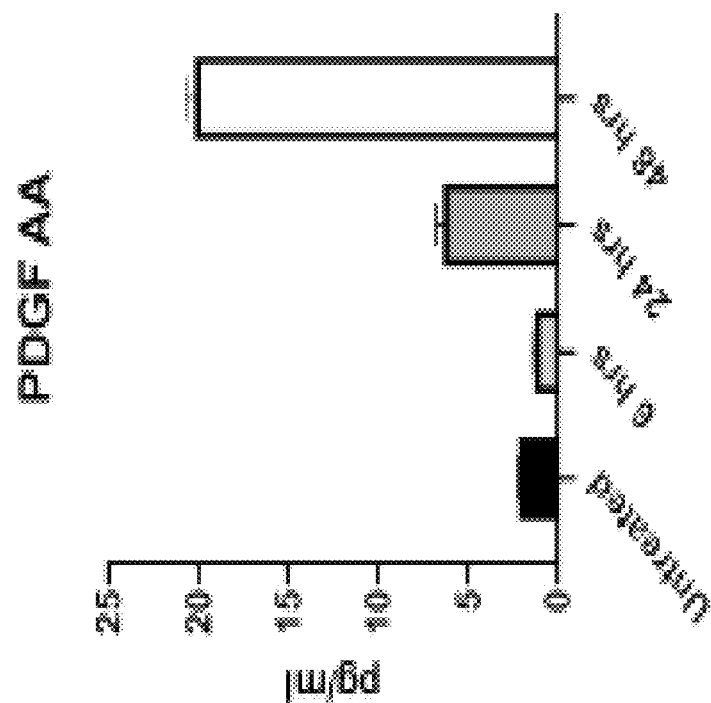
Figure 1I:
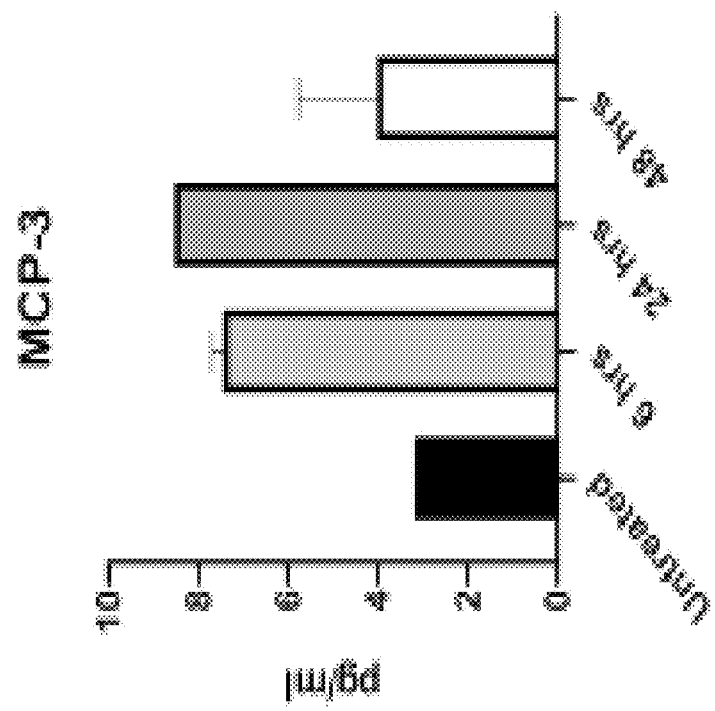
Figure 1L:
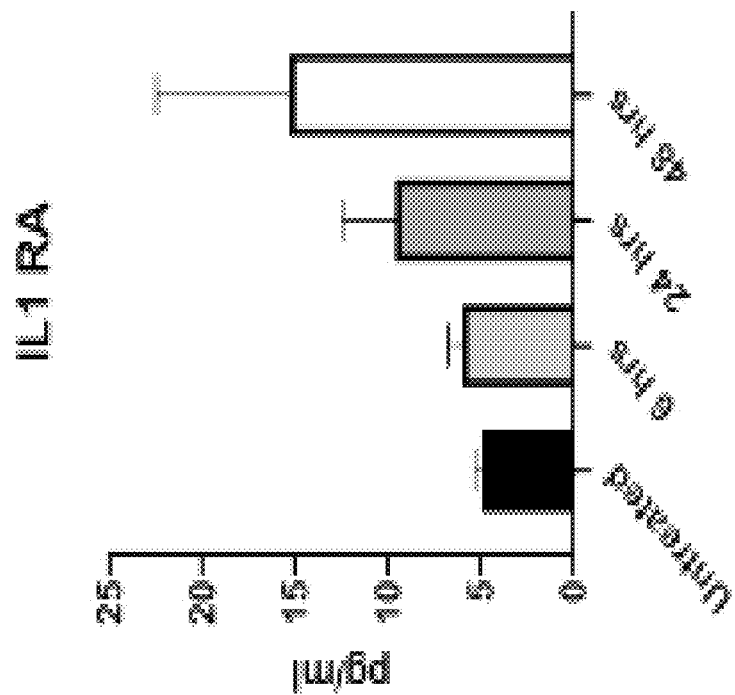
Figure 1K:
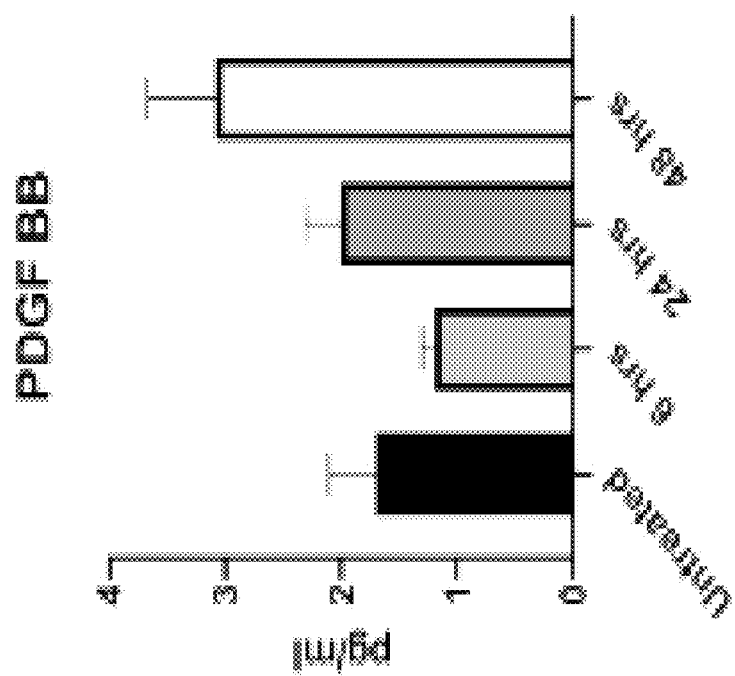
Figure 1N:
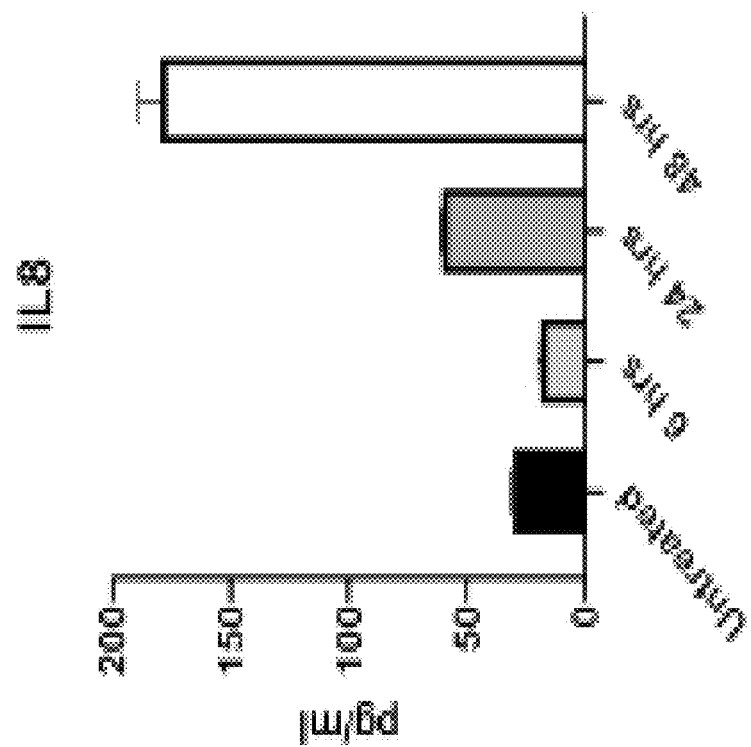
Figure 1M:
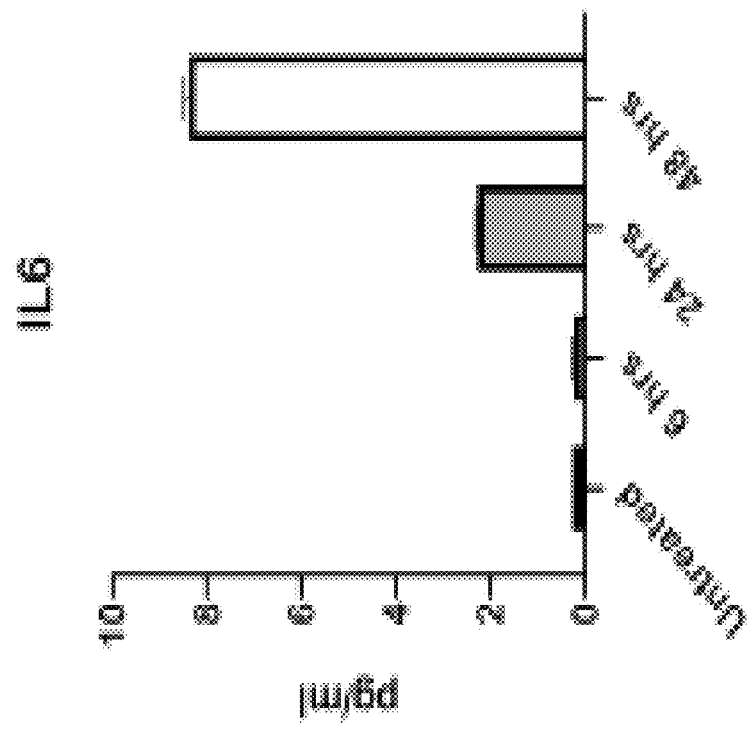
Figure 1P:
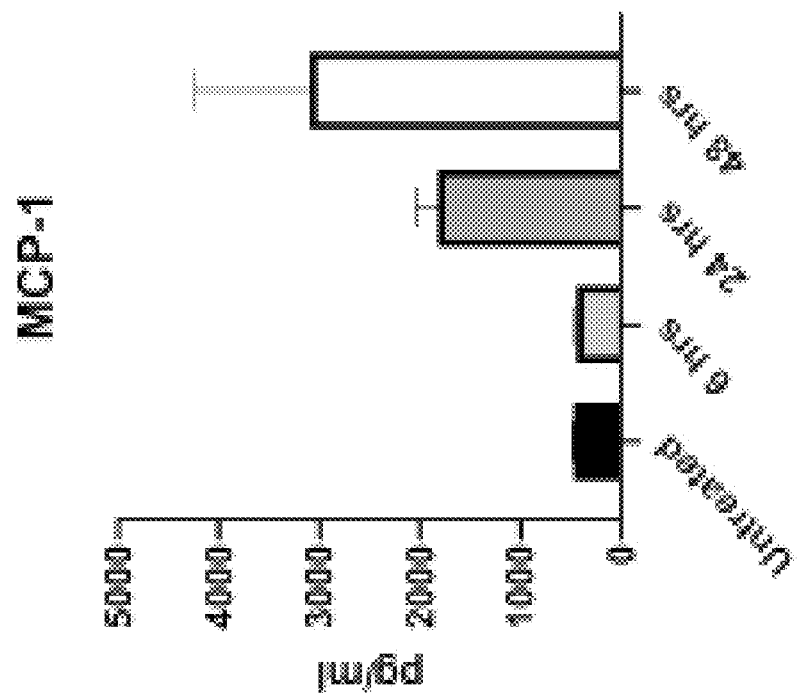
Figure 1O:
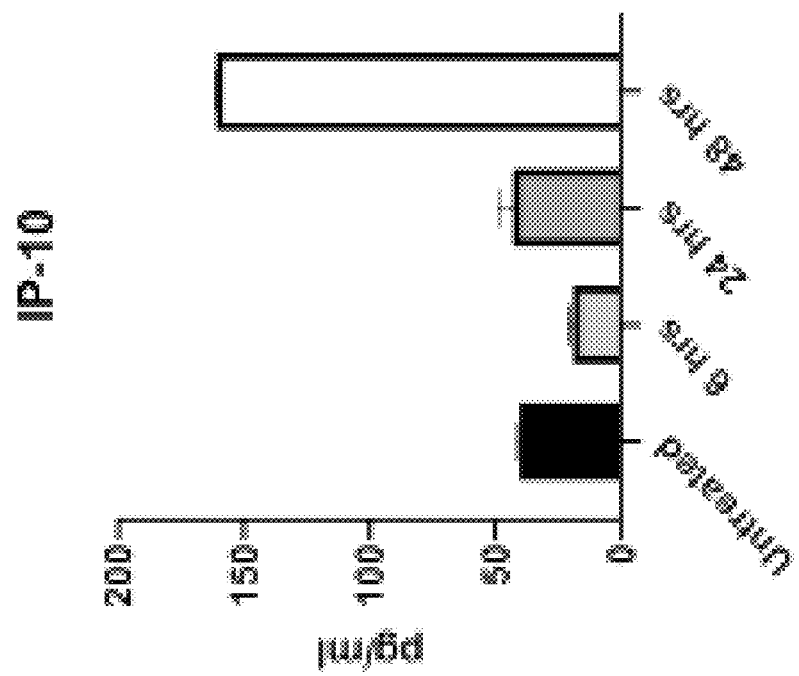
Figure 1Q:
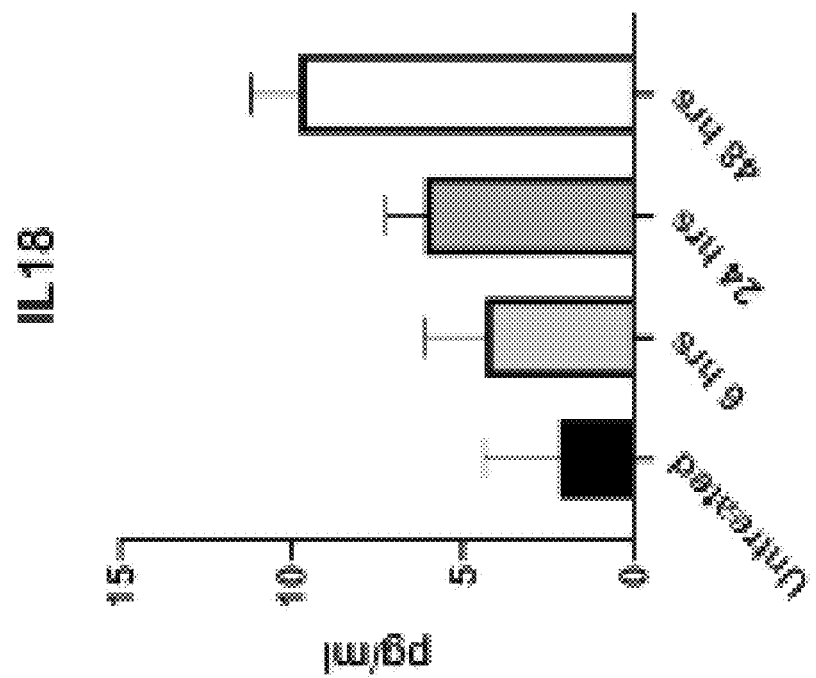
Figure 1R:
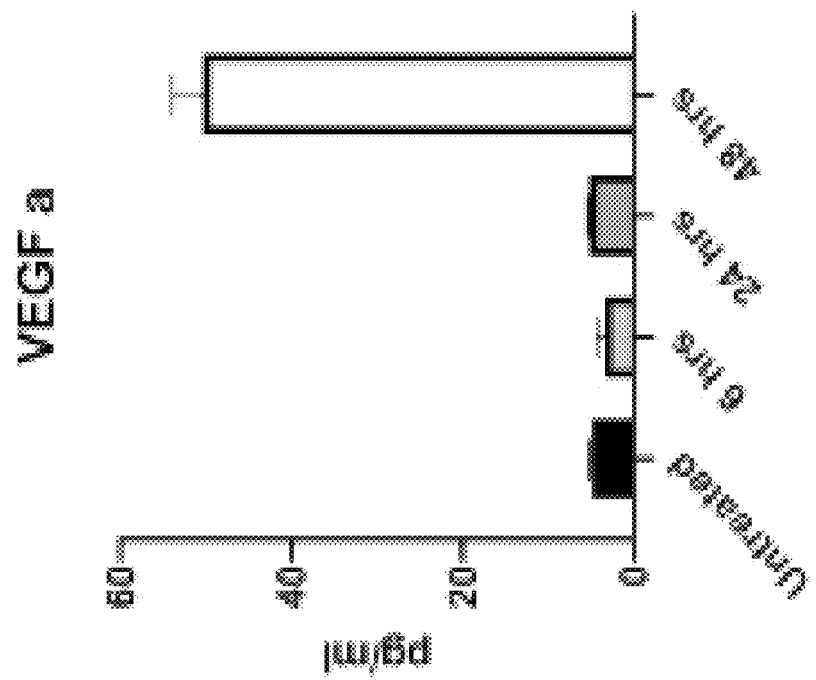

The chemokine assays showed specific upregulation of a distinct set of pro-inflammatory and cytotoxic T-cell recruitment cytokines (FIGS. 1C-1R). Thus, as shown, a peak in the induction of monocyte chemoattractant protein-3 (MCP-3) and IFN gamma was seen at 24 hours (>2 fold) and an approximately 10-fold increase in each of IL-6, IL-8 and interferon gamma-induced protein 10 (IP-10) was seen 24 hours following exposure to RB. A significant increase in MCP-1 levels was also noted.

These results demonstrate RB-induced STING dimerization and HSP association leading to an acute pro-inflammatory and immune response (i.e., within 24-48 hours). Additional in vitro studies confirmed that RB induces STING dimerization in solution (i.e., that the effect is not dependent on action within cancer cells).

The AML model and subsequent investigation illustrates that the HX compounds, such as for example RB, can induce acute STING dimerization. This has important implications in oncology where STING-mediated immune activation can play a pivotal role in innate and adaptive immune system response in anti-tumor therapy, either as a single-agent immunotherapy such as with injectable oncology drugs as described by Dees et al., U.S. Pat. No. 7,648,695, or where such drugs are used in combination therapy with other drugs as described by Eagle et al., U.S. Pat. No. 9,107,887.

These results also indicate that HX compound-based induction of STING dimerization has important implications in virology where STING-mediated immune activation can play a pivotal role in innate and adaptive immune system response in antiviral therapy, either as a single-agent antiviral drug or in combination therapy with other antiviral drugs. An adjuvant amount of an HX molecule or salt (compound), as previously discussed, is that amount that induces STING dimerization (i.e., a STING dimerization-inducing amount) and is further defined as an amount of HX compound that is less than a cytotoxic amount, and preferably less than about 75% of a cytotoxic amount. A cytotoxic amount is the $IC_{50}$ amount for an oncology indication (e.g., neuroblastoma, leukemia, melanoma or other tumor), whereas for infectious disease, the cytotoxic amount is the $IC_{50}$ for normal tissue (e.g., cultured fibroblasts, kidney cells, and the like).

The short human circulatory half-life of the HX compounds (about 30 minutes) facilitates effective application of these molecules for acute STING activation, maximizing innate immune signaling potential while avoiding chronic activation that could lead to counterproductive inflammatory response, possible autoimmune disease or promotion of tumorigenesis. As is seen from the in vitro results shown in FIGS. 1C-1R, the effects of RB on enhancing the cytokine production occurred within 48 hours in each of the sixteen cytokines.

Administration of one or more systemic doses can be particularly productive to initiate an immune response, especially in patients with reduced immune capacity. This approach is equally applicable to use of the HX compounds as an immune adjuvant for cancer or microbial infection as is discussed below.

Halogenated Xanthenes as Immunogen Adjuvants

An alternate, common approach for combating viral infection is the use of a vaccine. These medicaments are traditionally predicated on exposing a patient's immune system to moderated or inactivated virus or viral immunogens prior to exposure to live virus via infection. This procedure permits the patient to develop an adaptive immune response capable of preventing significant infection of tropic tissues upon exposure to virus.

Elucidation of the viral genome permits synthetic vaccine development to be undertaken based on modeling viral structure (i.e., surface proteins) to guide identification or synthesis of novel antiviral strategies [Graham et al., *Ann Rev Med* 70:91-104 (2019)]. Publication of the structure of the characteristic SARS-CoV-2 surface spike (S) glycoprotein provides an important target for this type of focused development [Wrapp et al., *Science* 367:1260-1263 (2020)].

This unique CoV spike protein provides an alternate target for disabling viral function (i.e., preventing attachment to tropic cells or viral unpacking and replication) or as an immune adjuvant by increasing the antigenicity of virus to the host immune system. Because the CoV surface spike is largely conserved across CoVs it is especially attractive as a potential broad-spectrum target for anti-CoV drug and vaccine development.

In particular, the extremely high affinity of RB and its HX compound analogs for glycoproteins conveys potential to: disable viral function by inhibiting attachment of CoV to tropic cells or by inhibiting viral unpacking and replication within infected cells; and as an immune adjuvant by increasing the antigenicity of virus to the host immune system upon complexation with viral surface glycoprotein structures, such as CoV surface spike (S) glycoprotein. Increased antigenicity can be used during early exposure to potentiate host immune response prior to onset of widespread infection.

Halogenated Xanthenes Provide Novel, Broad Applicability to Oncology and Virology The above discussion illustrates that RB and its HX compound analogs have novel roles in oncology and virology that have not been previously conceived or disclosed. Because of the effect this class of molecule has on STING dimerization, there is a role as an immune adjuvant in both oncology and virology. Furthermore, the high binding affinity for biomolecules and the unique chemical structure of the RB and other HX compounds as previously described lead to a role as a blocking agent against viral replication.

This affinity can also have applicability to blocking viral attachment through binding with viral peplomers (i.e., blocking cell receptor structures) or other viral surface structures. Because the halogen composition of HX compounds can be varied, 3-dimensional fit for a specific target can be optimized by varying halogen content (such as replacing one or more of the chlorine atoms at positions 4-, 5-, 6- or 7- with fluorine or bromine or a mixture thereof), and/or by replacing one or more of the iodine atoms at positions 2'-, 4'-, 5'- or 7'- with fluorine or bromine or a mixture thereof), or by aliphatic substitution at one or more of these positions. Alternately, this class of molecule can function to inhibit viral function (inhibiting attachment to tropic cells or viral unpacking and replication through complexation with viral surface spike glycoproteins or other viral surface structures or with host proteins in the viral interactome) or increase viral antigenicity via such complexation.

In addition to being a useful adjuvant for a vaccine that utilizes a SARS-CoV-2 surface spike glycoprotein polypeptide to be part of a vaccine against SARS-CoV-2, RB and other HX compounds can also be useful as adjuvants against other infectious agents such as other viruses, bacteria, fungi and single celled parasites, particularly using proteinaceous immunogens from those agents. Illustrative viruses include influenza, hepatitis viruses A, B, C and D, herpes viruses such as Varicella zoster (chickenpox), Herpes simplex 1 and 2 (HSV1 and HSV2), human papilloma virus (HPV), and the like. Illustrative bacterial pathogens include *E. coli, E. faecalis, S. aureus*, and the like. An illustrative unicellular parasite is the malaria sporozoite of *P. falciparum, P. vivax, P. bergeii* or *P. yoelli*. Illustrative fungal infective agents include *Candida albicans, Candida glabrata, Candida parapsilosis, Candida tropicalis*, and *Candida krusei*.

Illustrative proteinaceous immunogens and disease-related marker molecule peptides are disclosed in WO 2020028532 with citations to their published sources.

U.S. Pat. No. 6,942,866 includes the following peptidal epitopes:

Malarial B Cell Epitopes
 *P. falciparum*
 *P. vivax*
 *P. bergeii*
 *P. yoelli*

Malarial Universal T Cell Epitope
 *P. falciparum*
 *P. vivax*
 *P. yoelli*

U.S. Pat. No. 8,017,127 includes the following peptidal epitopes:

Influenza A M2 Protein B Cell Epitopes As is noted in U.S. Pat. No. 8,017,127, the M2 protein is expressed in cells infected by the influenza A strains. The N-terminal residues 1-24 of the M2 protein extends through the infected cell's membrane. That extracellular portion of the protein is referred to as M2e. Consequently, use of the influenza A extracellular M2e portion of that protein as the immunogenic marker can provide protection from all of the influenza strains. Thus, the yearly changes in influenza vaccine selection can be avoided.

U.S. Pat. No. 4,599,231 includes the following peptidal epitopes:

Hepatitis B Virus Surface Antigen

The hepatitis B virus surface antigen (HBsAg) provides both B cell and T cell polypeptide epitopes. A number of each epitope type as disclosed in U.S. Pat. No. 4,599,231 are set out below in the table along with their peptide denominations, and parenthesized sequence position from the N-terminus, as recited in that patent based on DNA from an ayw donor (P49) and an adw donor (P72 and P73).

B Cell Epitope

U.S. Pat. No. 5,180,806 includes the following epitopes:

Human Papilloma Virus (HPV) Marker Peptides

Papillomaviruses induce benign, dysplastic and malignant hyperproliferations of skin or mucosal epithelium. More than 50 types (strains) of human papillomavirus (HPV) have been identified. In humans, different papillomavirus types are known to cause distinct diseases. For example, HPV types 1 and 2 cause common warts, and types 6 and 11 cause condylomas and genital flat warts. In contrast, HPV types 16, 18 and 33 are carried in most cervical cancers and do not cause the usual condyloma, but rather persist diffusely in the cervical endothelium exhibiting only minimal pathologic changes. It is thought that the HPV types associated with cervical cancer are maintained in a latent state in cervical endothelium tissues for years after initial infection and then progress in some cases to cause cervical cancer.

U.S. Pat. No. 5,180,806 discloses several peptide sequences that induce the production of antibodies. Illustrative peptide markers of type 16-related HPV sequences disclosed in U.S. Pat. No. 5,180,806. That patent also discloses peptide sequences from type 18 and type 33, as well as sequences encoded by the E2 ORF of HPV types 6, 11, 18 and 33.

In Vivo Uses of the Halogenated Xanthenes

Data provided in Swift et al., *OncoTargets and Ther* 12: 1293-1307 (2019) illustrate that the concentration at which RB exerts half of its maximal inhibitory effect. (IC$_{50}$ value) against several pediatric solid tumor cancer cell lines (cultured SK-N-AS, SK—N—BE(2), rMR5, LAN1, SHEP, and SK—N—SH neuroblastoma cells, and SK-N-MC neuroepithelioma cells) in an in vitro cytotoxicity assay is in the range of 49 to 85 µM. These authors also reported that the IC$_{50}$ value of RB against normal, control cells (primary bone marrow and normal fibroblast) was 93 to 143 µM.

In vitro cell culture viability assays conducted using a panel of eleven commercially available leukemia cell lines derived from patients with either primary or relapsed pediatric leukemia that were treated with RB illustrated mean IC$_{50}$ values of 92.8 µM for the primary cell lines and 122.5 µM for the refractory cell lines. [Swift et al., *Blood*, 132, No. Suppl 1: 5207 (Nov. 21, 2018).]

The data provided herein also illustrate that STING dimerization is observed when THP-1 AMI cells are exposed to RB at a concentration of 100 µM; and that cytokine and chemokine production is observed in such cells upon such contact.

Based on a molecular weight of 1018 g/mole for disodium RB, the classic IV diagnostic use of RB, conducted by giving 100 mg RB as a single IV bolus to adults with a standard blood volume of approximately 5 L, achieved a concentration of approximately 20 mg/L in the blood, or approximately 20 µM RB. Exposure at such a level would have minimal direct cytotoxic effect on solid tumor or hematologic malignancies, as illustrated by the results of Swift et al. 2019 or Swift et al. 2018, above.

In clinical studies of PV-10 (10% disodium RB in saline for injection), RB has been tolerated at a bolus dose of 1500 mg upon intravasation when delivered intratumorally; this equates to an exposure of approximately 300 mg/L in the bloodstream (300 µM RB).

Thus, RB can be administered via a systemic route, such as intravenous (IV) infusion, at a level unlikely to elicit direct cytotoxicity of a significant fraction of tumor tissue (i.e., approximately 50 to 100 µM or lower) that can elicit STING dimerization (i.e., up to approximately 50 to 100 µM).

Avoidance of direct cytotoxicity to tumor cells can be preferable for avoiding a toxic reaction (i.e., tumor lysis syndrome) that can result from rapidly killed tumor cell burden. Howard et al., *N Engl J Med* 364(19):1844-1854 (May 12, 2011) report that tumor lysis syndrome is the most common disease-related emergency encountered by physicians treating hematologic cancers.

Due to the rapid clearance of RB from circulation in humans ($t_{1/2}$ about 30 minutes), continuous infusion can be used to maintain peak levels of RB in circulation (i.e., for up to several hours or more) during a single administration.

The short circulatory half-lives of the HX compounds facilitate effective application of these molecules for acute STING activation, maximizing innate immune system signaling potential while avoiding chronic activation that could lead to counterproductive inflammatory response and possibly autoimmune disease.

Administration of one or more systemic doses can be particularly productive to initiate an immune system response, especially in patients with reduced immune capacity. This approach is equally applicable to use of the HX compounds as an immunological adjuvant for cancer or microbial infection.

Systemic or regional administration can be achieved by IV administration, slow IV infusion, continuous IV infusion, oral administration, aerosol inhalation or establishment of a subcutaneous depot or similar means. Extended release from a depot can be achieved by complexing HX compounds with a non-absorbed or slowly absorbed carrier via a cleavable linkage, such as esterification to nanoparticles, an injectable filler, or similar carrier.

A mammalian subject having a microbial infection, such as a viral or bacterial infection, or cancer, such as leukemia, neuroblastoma, melanoma, non-small cell lung cancer and the like, in need of treatment (a mammalian subject) and to which a pharmaceutical composition containing an HX compound or its pharmaceutically acceptable salt or RB disodium can be administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

As noted above, it can be advantageous to avoid directly killing, via cytotoxicity, a substantial portion of cancerous cells during a single treatment. The present invention can therefore provide a means for initiation of a type I IFN immune response and downstream activation of an adaptive immune response with minimal risk of toxic reaction.

In addition to guiding dose selection for oncology, these concentration ranges establish metes and bounds for selection of clinical parameters for antiviral use of RB and related HX compounds. In particular, it is noted that concentrations of 300 µM and lower are tolerated, with concentrations of 100 µM and lower preferred to avoid potential onset of toxicity to normal tissue.

The similarly useful halogenated xanthene compounds listed below and their pharmaceutically acceptable salts can have molecular weights that differ from each other by about a factor of three (See, Table 3, U.S. Pat. No. 7,390,668 at columns 15-16). It is preferred that an exact amount of a specific HX compound to be used is calculated based on molecular weights for each such compound or that of RB.

A contemplated HX compound includes rose bengal (4,5,6,7-tetrachloro-2',4',5',7'-tetraiodo-fluorescein; RB) that is particularly preferred, erythrosin B, phloxine B, 4,5,6,7-tetrabromo-2',4',5',7'-tetra-iodofluorescein, 2',4,5,6,7-pentachloro-4',5',7'-triiodofluorescein, 4,4',5,6,7-pentachloro-2',5',7'-triiodofluorescein, 2',4,5,6,7,7'-hexachloro-4',5'-diiodofluorescein, 4,4',5,5',6,7-hexachloro-2',7'-diiodofluorescein, 2',4,5,5',6,7-hexachloro-4',7'-diiodofluorescein, 4,5,6,7-tetrachloro-2',4',5'-triiodofluorescein, 4,5,6,7-tetrachloro-2',4',7'-triiodofluorescein, 4,5,6,7-tetrabromo-2',4',5'-triiodofluorescein, and 4,5,6,7-tetrabromo-2',4',7'-triiodofluorescein.

The reader is directed to Berge, *J. Pharm. Sci.* 1977 68(1):1-19 for lists of commonly used pharmaceutically acceptable acids and bases that form pharmaceutically acceptable salts with pharmaceutical compounds, such as the above halogenated xanthenes. Illustrative cations include alkali metals such as sodium, potassium, as well as ammonium and alkaline earth salts such as magnesium and calcium. The disodium salt of rose bengal is particularly preferred.

A $C_1$-$C_4$ alkyl ester of one of the above halogenated xanthene compounds can also be used, with the $C_2$; i.e., ethyl ester, being preferred. Thus, in vitro studies using each of RB, ethyl-Red 3 (erythrosine ethyl ester; 2',4',5',7'-tetraiodo-fluorescein ethyl ester), 4,5,6,7-tetrabromo-2',4',5',7'-tetraiodofluorescein and ethyl-Phloxine B (4,5,6,7-tetrachloro-2',4',5',7'-tetrabromofluorescein ethyl ester) exhibited similar anti-tumor activities against CCL-142 renal adenocarcinoma. When an aromatic ester is used, it is preferably a benzyl or phenyl ester.

The carboxyl group of an HX compound can also be used to form an amide group. The amide nitrogen atom can be unsubstituted [—C(O)—$NH_2$], monosubstituted with a $C_1$-$C_4$ alkyl group [—C(O)—$NHR^1$, where $R^1$ is $C_1$-$C_4$ alkyl], or be disubstituted with two independently selected $C_1$-$C_4$ alkyl groups, [—C(O)—$NR^1R^2$, where $R^1$ and $R^2$ are each independently the same or different $C_1$-$C_4$ alkyl groups]. Alternatively, the $R^1$ and $R^2$ groups together with the amido nitrogen atom form a 5- or 6-membered ring.

Additionally, the HX compound carboxyl group can form an aromatic derivative that is an ester or monosubstituted amide. The aromatic ring of such a derivative is a single 5- or 6-membered aromatic ring, or a 5,6- or 6,6-fused aromatic ring system that contains 0, 1 or 2 hetero ring atoms that are independently nitrogen, oxygen or sulfur.

An aromatic derivative whose aromatic ring portion is phenyl, benzyl or 2-, 3-, or 4-pyridyl (pyridyl) is presently preferred. However, other aromatic single and fused ring-containing esters and amides are contemplated. Illustrative examples of such aromatic ester and amide derivative groups are shown and named below, wherein Z is O or NH, line-Z indicates the ring-oxygen or ring-nitrogen can be from any available carbon of the ring, and Z-line crossed by a wavy line indicates that the depicted alkoxy or amino group is a portion of another molecule, the esterified or amidified HX molecule.

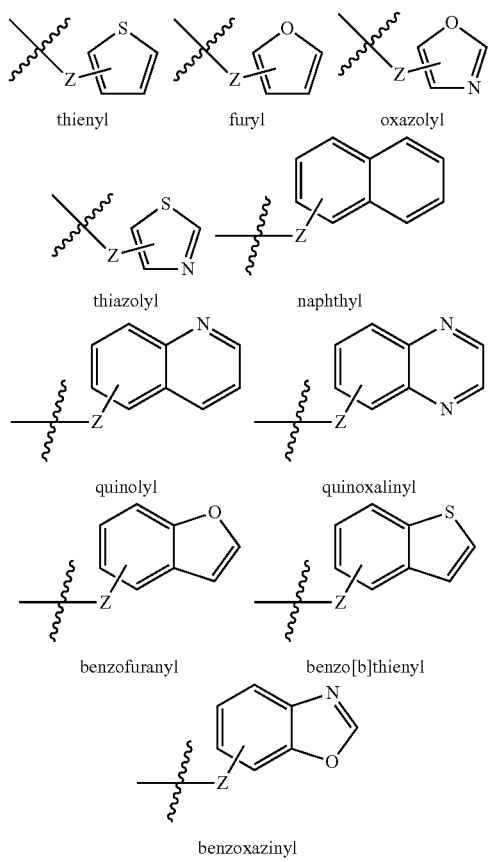

An aliphatic or aromatic derivative of one of the above HX compounds can also be used, such as 2,3,4,5-tetrachloro-6-(6-hydroxy-2,4,5-triiodo-7-isopropyl-3-oxo-3H-xanthen-9-yl)benzoic acid disodium [4,5,6,7-tetrachloro-2',4',5'-triiodo-7'-isoproplyfluorescein], represented by Figure is in Singer et al. U.S. Pat. No. 8,530,675, and similar aliphatic or aromatic derivatives formed via attachment of one or more aliphatic or aromatic moieties at one or more of positions 2, 3, 4, 5, 2', 4', 5' or 7'.

A preferred form of RB is rose bengal disodium that has the structural formula below:

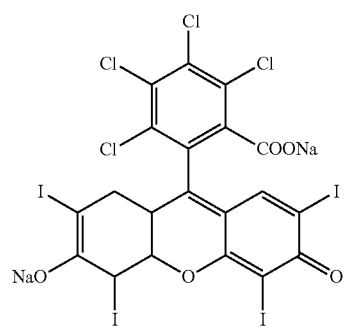

Further details of the medicinal use a pharmaceutical composition containing an above-noted HX compounds are described in U.S. Pat. Nos. 5,998,597, 6,331,286, 6,493,570, 7,390,668, 7,648,695, 8,974,363, 9,107,887, 9,808,524, 9,839,688, 10,130,658 and 10,471,144, whose disclosures are incorporated by reference herein in their entireties.

A contemplated HX or its pharmaceutically acceptable salt is typically used dissolved or dispersed in an aqueous pharmaceutical composition. The HX compound is typically present at 0.1 to about 20% (w/v) in an aqueous 0.9% saline pharmaceutical composition.

Because a contemplated pharmaceutical composition is typically intended for parenteral administration as by an IV method, such a composition should contain an electrolyte, and preferably have approximately physiological osmolality and pH value. A preferred concentration of singly charged electrolyte ions in a pharmaceutically acceptable aqueous medium is about 0.5 to about 1.5% (w/v), more preferably at about 0.8 to about 1.2% (w/v), and most preferably at a concentration of about 0.9% (w/v). The about 0.9% (w/v) concentration is particularly preferred because it corresponds to an approximately isotonic aqueous solution. In a further preferred embodiment, the electrolyte in a contemplated pharmaceutical composition is sodium chloride.

Electrolytes at such levels increase the osmolality of a pharmaceutically acceptable aqueous medium. Thus, as an alternative to specifying a range of electrolyte concentrations, osmolality can be used to characterize, in part, the electrolyte level of the composition. It is preferred that the osmolality of a composition be greater than about 100 mOsm/kg, more preferably that the osmolality of the composition be greater than about 250 mOsm/kg, and most preferably that it be about 300 to about 500 mOsm/kg.

It is preferred that the pH value of a pharmaceutically acceptable aqueous medium be about 4 to about 9, to yield maximum solubility of the HX compound in an aqueous vehicle and assure compatibility with biological tissue. A particularly preferred pH value is about 5 to about 8, and more preferably between about 6 to about 7.5. At these pH values, the halogenated xanthenes typically remain in dibasic form, rather than the water-insoluble lactone that forms at low pH values.

The pH value of a pharmaceutically acceptable aqueous medium can be regulated or adjusted by any suitable means known to those of skill in the art. The composition can be buffered or the pH value adjusted by addition of acid or base or the like. As the halogenated xanthenes, or physiologically acceptable salts thereof, are weak acids, depending upon halogenated xanthene concentration and/or electrolyte concentration, the pH value of the composition may not require the use of a buffer and/or pH modifying reagent. It is especially preferred, however, that the composition not contain any buffer (be free of buffer or buffer-free), permitting it to conform to the biological environment once administered.

Alternate contemplated pharmaceutical compositions adapted for oral administration, inhalation, or other non-parenteral routes of administration, can be formulated and delivered using methods standard in the art for such routes of administration.

In the present invention, the specific amount of HX compound such as RB or RB disodium administered is not believed to be as important as was the case where the composition was injected intratumorally to a tumor because the object here is to ultimately provide a therapeutically active concentration of HX compound to the environment of the diseased cells and in which those diseased cells can be contacted with the HX compound at sufficient level to elicit a therapeutic effect, either via STING activation or antiviral activity dependent upon the specific indication.

A second therapeutic agent useful for combination treatment with an HX compound in anti-viral indication is an antibody or mixture of antibodies (sometimes referred to as an "antibody cocktail"). Illustrative of such antibodies are monoclonal antibodies that immunoreact with the viral spike protein and thereby inhibit binding of the virus to a human cell. These monoclonal antibodies are administered by infusion.

One antibody immunoreactive to the viral spike protein, the monoclonal antibody, bamlanivimab, had Emergency Use Authorization (EUA) from the FDA as a single agent lifted on Mar. 17, 2021 in the states of California, Arizona and Nevada due to the presence there of the so-called "California" variant resistant to bamlanivimab (mutational escape). A spokesman for the manufacturer, Eli Lilly and Company reported that same day that when bamlanivimab is used with the monoclonal antibody etesevimab, the neutralizing effect against that variant was maintained.

Another pair of spike protein-reactive monoclonal antibodies, casirivimab and imdevimab, sold under the trade name REGN-COV by Regeneron Pharmaceuticals received its EUA from the U.S. Food and Drug Administration on Nov. 21, 2020. These monoclonal antibodies immunoreact with the viral spike protein at two different positions, and when so bound, block the virus from entering the body's cell. These monoclonal antibodies are administered in a mixture that contains equal amounts of each.

Because an HX compound can complex with viral spike protein, as shown infra, combination of an HX compound with such spike protein-reactive monoclonal antibodies can augment antiviral activity by further interfering with viral binding, thereby increasing therapeutic activity of such antibodies and hinder mutational escape.

Intact monoclonal antibodies, as well their paratope-containing portions (binding site-containing portions) such as Fab, Fab', F(ab')$_2$ and Fv regions, as well as single-stranded antibody peptide binding sequences can be useful. Intact humanized monoclonal antibodies have half-lives in a human body of about one to three weeks as can be seen from the package inserts. Using immune checkpoint inhibitors as illustrative, e.g., Yervoy® (ipilimumab) terminal $t_{1/2}$=15.4 days; package insert 12/2013; Keytruda® (pembrolizumab) terminal $t_{1/2}$=23 days; package insert 03/2017]. Single-stranded antibody binding site oligo or polypeptides tend to have shorter half-lives in vivo.

Medicaments such as remdesivir and the monoclonal antibodies discussed above are administered in the amounts, under the conditions and with the timing stated in the instructions given in their FDA-approved package inserts. Those amounts are deemed to be effective amounts. For example, and in shortened form, for persons 12 years old and older weighing at least 40 kg, remdesivir is administered as a single loading dose of 200 mg on day 1, followed by once-daily maintenance doses of 100 mg from day 2 infused over 30-120 minutes. For patients not requiring invasive mechanical ventilation and/or extracorporeal membrane oxygenation (ECMO), the recommended total treatment duration is 5 days. That time-period can be extended for up to 5 days if the patient does not demonstrate clinical improvement.

The HX compound is administered on the same day as the remdesivir or the monoclonal antibody as discussed above. Both medicaments, the HX compound such as RB and the monoclonal antibodies are preferably administered in separate compositions. It is preferred to administer both types of medicament within minutes to about 8 hours of each other. More preferably, both are administered within less than one hour of the other. Put differently, the two types of medicament are administered on overlapping schedules, preferably within one hour of each other.

As used herein, "administration" is used to mean the beginning of a treatment regimen. Thus, swallowing a tablet or other per os dosage form is the beginning of a treatment regimen, as is the time at which an IV flow is begun. When both first and second anticancer agents are present together in the same, single composition, administration begins when that unitary composition enters the subject's body.

Methodology and Results

Computer Modeling for Complex Formation

Computer models were prepared using the AutoDock Vina [Dr. Oleg Trott, Molecular Graphics Lab, Scripps Research Institute, La Jolla, CA] and BIOVIA Discovery Studio [Dassault Systèmes BIOVIA, Discovery Studio Modeling Environment, Release 2017, San Diego, CA] platforms to perform in silico flexible ligand-receptor docking and determine overall binding energy based on interatomic distances.

Based on the previously discussed findings relating to FIGS. 6A-6C, a set of studies was designed to provide some aspects of specificity behind these data, using assays based on quantitative polymerase chain reaction (qPCR) of viral RNA (vRNA) coding for viral envelope protein (E gene product). In these studies, virus was pre-incubated with RB before the addition to the cells. The experimental conditions are described in Table 1, below.

TABLE 1 qPCR treatment outlines

Pre-treatment of cells:
Pre-treat cells with RB (0.6 µM, 1 hour),
remove RB, add virus (1 hour), wash cells,
add growth medium
Pre-treatment of virus:
Pre-treat virus with RB (0.6 µM, 1 hour),
add virus + RB mixture to cells (1 hour),
wash cells, add growth medium
Virus + RB adsorption:
Add virus + RB to cells (1 hour), wash
cells, add growth medium
Normal:
Add virus to cells (1 hour), wash cells, add
RB/growth medium
Add RB post-adsorption:
Add virus to cells (1 hour), remove virus,
add growth medium (1 hour), remove, add
RB/growth medium (2 hours)
(+) control:
Add virus to cells (1 hour), wash cells, add
growth medium.
All conditions incubated for 16 hours, after
which viral sups were harvest, VRNA
extracted, and qPCR performed Following inhibition, cellular viral E gene expression was measured for copy numbers by PCR. Results presented in FIG. 7B show that lower copy numbers were seen when the virus was pre-treated with RB, possibly giving a head start in the binding to the areas of the virus that are blocked before subsequent interaction with the cellular receptors. ($p<0.05$).

Addition of virus and RB at the same time still showed a reduction compared to control but the reduction was less, indicating the possibility that RB at least in part interacts with a viral component. This is further confirmed by the observation that adding RB after the virus has been incubated with the cells had no effect, thereby confirming the reduction in E gene copy numbers are mediated by RB interaction with the virus in such a way that it interferes with subsequent viral attachment and replication.

Figure 7A:
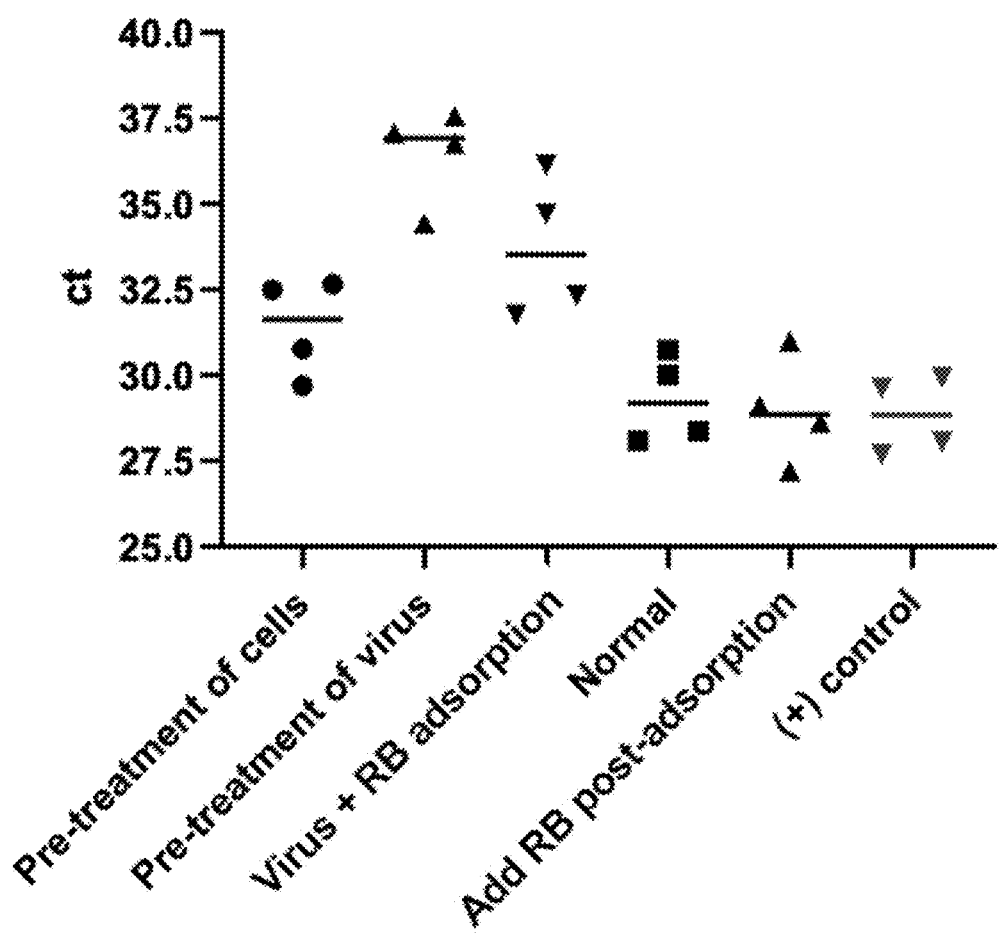
FIG. 7A is a graph of data showing cycle threshold (ct), the number of cycles of reverse transcription needed to amplify viral nucleic acid and thus an indicator of the amount of virus present; the data show higher ct values for virus treated with 0.6 μM RB under various conditions prior to or during viral absorption and a reduction of viral production compared to control; adding RB after the virus has been incubated with the cells had no effect on viral production. The reduction in gene copy numbers mediated by RB interaction with the virus in such way to interfere with subsequent viral attachment and replication is further evidenced by the data of FIG. 7B, showing number of viral copies.
Figure 7B:
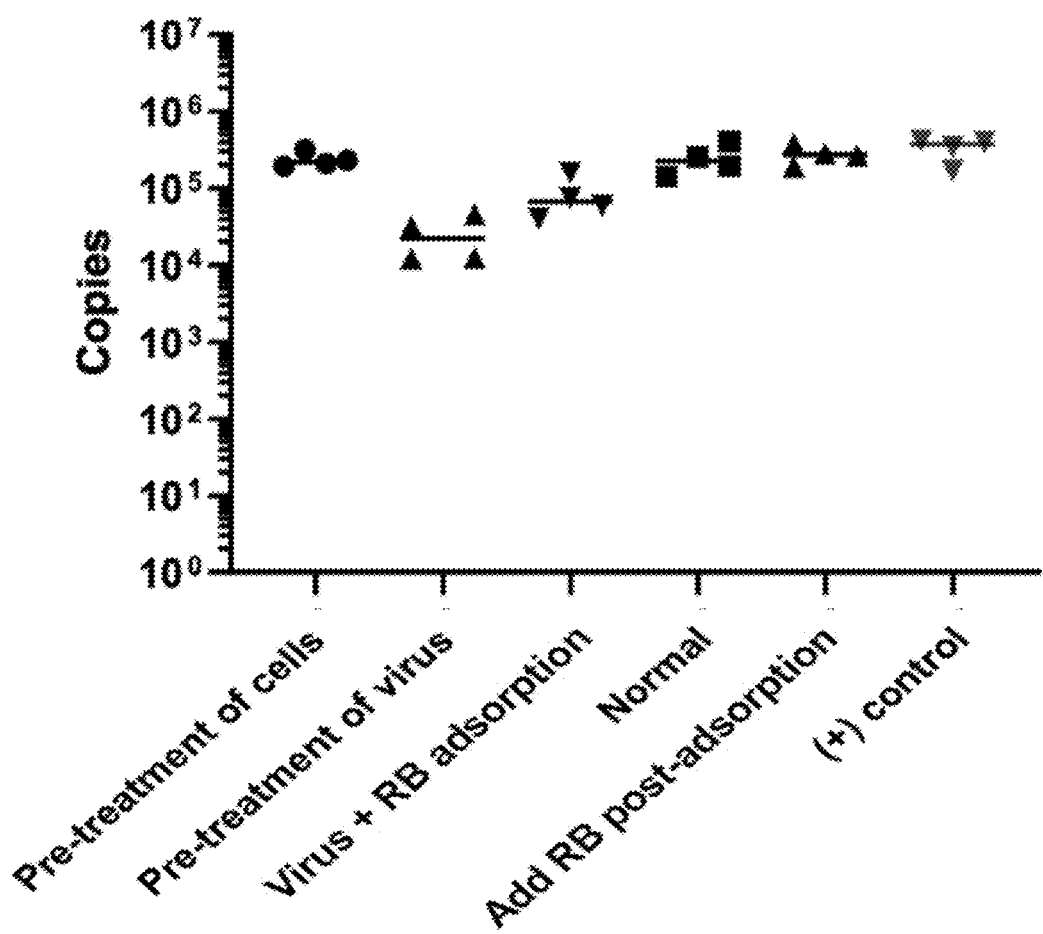

As a control, the level of sub-genomic viral RNA was examined at 16 hours post infection before the new virus had a chance to reproduce (FIG. 7A). The cycle threshold (ct, the number of cycles of reverse transcription needed to amplify viral nucleic acid) is an indicator of the amount of virus present and the data show higher ct values for virus treated with RB, confirming the trend seen in the direct measurement results presented in FIG. 7B and that RB adversely affected viral replication. Studies are in progress with increased RB concentrations and incubation times to see if better efficiency in blocking viral infectivity is achieved.

Materials and Methods

Vero C1008 cells (ATCC® CRL_1586™) were maintained in the recommended growth medium (Eagle's Minimum Essential Medium (ATCC® 30_2003™) supplemented with 10% FBS (ATCC® 30-2020™) 10 units Penicillin/10 µg/ml Streptomycin (Gibco™ 15140148) at 37° C. with 5% $CO_2$. Severe acute respiratory syndrome coronavirus 2 (SARS-CoV-2) isolate USA-WA1/2020 was obtained from BEI Resources (NR-52281).

Plaque Reduction Assay

Cells were seeded in growth medium supplemented with 10% FBS at a concentration of $4\times10^5$ cells/well (2 ml/well) in 6-well plates (Falconm 353046) and incubated overnight (about 18 hours) at 37° C. with 5% $CO_2$.

To test SARS-CoV-2 susceptibility to remdesivir (GS-5734™, MedKoo Biosciences, Inc.), growth medium was removed, cells were washed once with PBS (Corning™ 21031CV) and infected with about 60 plaque-forming units (PFU) of SARS-CoV-2 in growth medium supplemented with 2% FBS, in triplicates. After incubation for 1 hour with shaking every 15 minutes, SARS-CoV-2 was removed and cells were subsequently covered with 3 ml of medium containing 0.4% microcrystalline cellulose and DMSO or increasing amounts of remdesivir (0.156, 0.312, 0.625, 1.25, and 2.5 µM) and incubated at 37° C. with 5% $CO_2$. After incubation for 96 hours to allow for plaque formation, the overlay was removed and the cell monolayers were fixed with 10% buffered formalin phosphate (1 ml; Fisher SF100) for 1 hour, washed once with water and stained with 1% crystal violet (600 µl; Sigma C3886, diluted in 20% methanol) for 10 minutes. After crystal violet removal, cells were washed once with water and plaques were counted.

To assess the therapeutic effect of RB against SARS-CoV-2 in combination with remdesivir, drugs were applied sequentially after infection, first RB, followed by a fixed dose of remdesivir. Cells were washed once with PBS and infected with approximately 60 PFU of SARS-CoV-2 in growth medium supplemented with 2% FBS. After incubation for 1 hour with shaking every 15 minutes, SARS-CoV-2 was removed and 2 ml of medium was added containing RB at 1, 5, 20 and 50 µM and appropriate controls (0.9% saline or medium only), in triplicates. After incubation for 2 hours, RB was removed, cells were washed once with PBS and covered with 3 ml of medium containing 0.4% microcrystalline cellulose and 0.15 µM remdesivir or DMSO. After incubation for 96 hours to allow for plaque formation, plaques were visualized as described above. This assay was performed in duplicate.

To better mimic RB treatment of SARS-CoV-2 in vivo infection, RB was applied continuously during infection (pre-infection treatment of the cells, during infection and post-infection treatment until the end of the study). Cells were washed and incubated with 2 ml of medium containing increasing concentrations of RB and controls (medium only or 0.9% saline) for 2 hours, in triplicates.

Concentrations of 0.5, 1, 5, 10, 20, 50, 75, and 100 µM RB were tested for the first replicate and were adjusted to 0.5, 1, 5, 10, 20, 30, 40, and 50 µM for the second replicate.

Medium was removed then a mixture of RB and approximately 60 PFU of SARS-CoV-2 were added for 1 hour, shaking every 15 minutes. Afterwards, the virus-drug mixture was removed and replaced with RB-containing overlay. After incubation for 96 hours to allow for plaque formation, plaques were visualized as described above.

As a positive control, 5 µM remdesivir was added to the wells during infection with SARS-CoV-2 and in the overlay for 96 hours. This assay was performed in duplicate.

All steps with RB were performed in the presence of a red light. $IC_{50}$ and $EC_{50}$ values were calculated by the GraphPad Prism 8.0 software (non-linear regression analysis).

The articles "a" and "an" are used herein to refer to one or to more than one (i.e., to at least one) of the grammatical object of the article. By way of example, "an element" means one element or more than one element. Each of the patents, patent applications and articles cited herein is incorporated by reference.

The invention claimed is:

1. A method for treating a Sars-CoV-2 virus infection of a mammalian subject in need thereof that comprises administering an effective amount of Sars-CoV-2 virus-complexing halogenated fluorescein (HX), a pharmaceutically acceptable salt, an amide thereof whose nitrogen atom is unsubstituted, substituted with one or two $C_1$-$C_4$ alkyl groups that are the same or different or together with the amido nitrogen form a 5- or 6-membered ring, a $C_1$-$C_4$ alkyl ester thereof, an aromatic derivative thereof, wherein the aromatic derivative is an ester or amide formed from an alcohol or monosubstituted amine having a 5- or 6-membered aromatic ring, or a 5,6- or 6,6-fused aromatic ring system that contains 0, 1 or 2 hetero ring atoms that are independently nitrogen, oxygen or sulfur to said mammalian subject.

2. The method according to claim 1, wherein said HX is rose bengal disodium.

3. The method according to claim 1, wherein said administration is repeated.

4. A method of inducing type I interferon (IFN) response in a mammalian subject that presents with a microbial infection that comprises administering an amount of a halogenated fluorescein (HX), a pharmaceutically acceptable salt, an amide thereof whose nitrogen atom is unsubstituted, substituted with one or two $C_1$-$C_4$ alkyl groups that are the same or different or together with the amido nitrogen form a 5- or 6-membered ring, a $C_1$-$C_4$ alkyl ester thereof, an aromatic derivative thereof, wherein the aromatic derivative is an ester or amide formed from an alcohol or monosubstituted amine having a 5- or 6-membered aromatic ring, or a 5,6- or 6,6-fused aromatic ring system that contains 0, 1 or 2 hetero ring atoms that are independently nitrogen, oxygen or sulfur, effective to induce STING dimerization.

5. The method according to claim 4, wherein said HX is rose bengal disodium.

6. The method according to claim 4, wherein said mammal is a human.

7. The method according to claim 4, wherein said $C_1$-$C_4$ alkyl ester is a $C_2$ ester.

8. The method according to claim 4, wherein said microbial infection is a viral infection.

9. The method according to claim 4, wherein said microbial infection is a bacterial infection.

10. The method according to claim 4, wherein said microbial infection is a fungal infection.

11. A method of inducing type I interferon (IFN) response in a mammalian subject having a cancerous tumor that comprises systemically administering an amount of a halogenated fluorescein (HX), a pharmaceutically acceptable salt, an amide thereof whose nitrogen atom is unsubstituted, substituted with one or two $C_1$-$C_4$ alkyl groups that are the same or different or together with the amido nitrogen form a 5- or 6-membered ring, a $C_1$-$C_4$ alkyl ester thereof, an aromatic derivative thereof, wherein the aromatic derivative is an ester or amide formed from an alcohol or monosubstituted amine having a 5- or 6-membered aromatic ring, or a 5,6- or 6,6-fused aromatic ring system that contains 0, 1 or 2 hetero ring atoms that are independently nitrogen, oxygen or sulfur, effective to induce STING dimerization.

12. The method according to claim 11, wherein said HX is rose bengal disodium.

13. The method according to claim 11, wherein said mammalian subject is a human.

14. The method according to claim 11, wherein said $C_1$-$C_4$ alkyl ester is a $C_2$ ester.

15. A method of inducing type I interferon (IFN) response in a mammalian subject having a hematologic malignancy that comprises systemically administering a less than cytotoxic amount of a halogenated fluorescein (HX), a pharmaceutically acceptable salt, a $C_1$-$C_4$ alkyl ester, or other aliphatic or aromatic derivative thereof, an amide thereof whose nitrogen atom is unsubstituted, substituted with one or two $C_1$-$C_4$ alkyl groups that are the same or different or together with the amido nitrogen form a 5- or 6-membered ring, a $C_1$-$C_4$ alkyl ester thereof, an aromatic derivative thereof, wherein the aromatic derivative is an ester or amide formed from an alcohol or monosubstituted amine having a 5- or 6-membered aromatic ring, or a 5,6- or 6,6-fused aromatic ring system that contains 0, 1 or 2 hetero ring atoms that are independently nitrogen, oxygen or sulfur, to said mammalian subject that is effective to induce STING dimerization.

16. The method according to claim 15, wherein said HX is rose bengal disodium.

17. The method according to claim 15, wherein said mammalian subject is a human.

18. The method according to claim 15, wherein said $C_1$-$C_4$ alkyl ester is a $C_2$ ester.

19. A method of enhancing a mammalian immunogen-specific immune response that comprises contacting mammalian cells present in vivo with an adjuvant-effective amount of a halogenated fluorescein (HX), a pharmaceutically acceptable salt, an amide thereof whose nitrogen atom is unsubstituted, substituted with one or two $C_1$-$C_4$ alkyl groups that are the same or different or together with the amido nitrogen form a 5- or 6-membered ring, a $C_1$-$C_4$ alkyl ester thereof, an aromatic derivative thereof, wherein the aromatic derivative is an ester or amide formed from an alcohol or monosubstituted amine having a 5- or 6-membered aromatic ring, or a 5,6- or 6,6-fused aromatic ring system that contains 0, 1 or 2 hetero ring atoms that are independently nitrogen, oxygen or sulfur, and an immunogen to which said response is to be enhanced.

20. The method according to claim 19, wherein said halogenated fluorescein is rose bengal disodium.

21. The method according to claim 19, wherein said immunogen is a viral proteinaceous peptide sequence.

22. A method for treating a SARS-CoV-2 virus infection of a mammalian subject in need thereof that comprises administering an effective amount of whole antibodies or paratope-containing portions thereof that bind to the SARS-CoV-2 virus spike protein and a SARS-CoV-2 virus-complexing amount of a halogenated fluorescein (HX) compound, a pharmaceutically acceptable salt, an amide thereof whose nitrogen atom is unsubstituted, substituted with one or two $C_1$-$C_4$ alkyl groups that are the same or different or together with the amido nitrogen form a 5- or 6-membered ring, a $C_1$-$C_4$ alkyl ester thereof, an aromatic derivative thereof, wherein the aromatic derivative is an ester or amide formed from an alcohol or monosubstituted amine having a 5- or 6-membered aromatic ring, or a 5,6- or 6,6-fused aromatic ring system that contains 0, 1 or 2 hetero ring atoms that are independently nitrogen, oxygen or sulfur, to said mammalian subject.

23. The method of claim 22, wherein said HX compound or its pharmaceutically acceptable salt is rose bengal or rose bengal disodium.

24. The method according to claim 22, wherein said antibodies are whole antibodies.

25. The method of any of claims 1, 3, 4, 6, 8-11, 13, 15, 17, 19, 22, or 24, wherein said aromatic derivative is an ester or amide formed from an alcohol or monosubstituted amine that is selected from the group consisting of one or more of benzyl, phenyl, pyridyl, thienyl, furyl, oxazolyl, thiazolyl, naphthyl, quinolyl, quioxalinyl, benzofuranyl, benzo[b]thienyl and benzoxazinyl alcohols or amines.

\* \* \* \* \*